(12) United States Patent
Liao et al.

(10) Patent No.: US 6,855,822 B2
(45) Date of Patent: Feb. 15, 2005

(54) BENZO[B]FURAN DIMERS

(75) Inventors: Yun Liao, Glen Rock, NJ (US); Reza Fathi, Hohokus, NJ (US); Zhen Yang, Ridgewood, NJ (US)

(73) Assignee: VivoQuest, Inc., Valley Cottage, NY (US)

( * ) Notice: Subject to any disclaimer, the term of this patent is extended or adjusted under 35 U.S.C. 154(b) by 1 day.

(21) Appl. No.: 10/602,341

(22) Filed: Jun. 23, 2003

(65) Prior Publication Data

US 2004/0110949 A1 Jun. 10, 2004

Related U.S. Application Data

(60) Provisional application No. 60/391,100, filed on Jun. 24, 2002.

(51) Int. Cl.[7] .................. C07D 241/02; C07D 303/38; C07D 405/00

(52) U.S. Cl. ................... 544/376; 546/284.1; 549/294; 549/466

(58) Field of Search ................ 544/376; 546/284.1; 549/294, 466

(56) References Cited

PUBLICATIONS

Liao, Y. et al. "Convergent Solid–Phase Synthesis of Symmetrical Benzo[b]furan's Dimerizer", *Journal of Combinatorial Chemistry*, vol. 5, No. 2, Mar. 2003, p. 79–81.

*Primary Examiner*—Taofiq Solola
(74) *Attorney, Agent, or Firm*—Kenyon & Kenyon

(57) ABSTRACT

Benzo[b]furan dimers and processes for their preparation are provided. The invention provides a synthetic process for the preparation of benzo[b]furan dimer using mild reaction conditions, which provides a high substituent tolerance and is appropriate for use in solid phase syntheses for producing a library of benzo[b]furan dimers for biological screening.

3 Claims, No Drawings

BENZO[B]FURAN DIMERS

This application claims the benefit of Provisional Application No. 60/391,100, filed Jun. 34, 2002.

FIELD OF THE INVENTION

The present invention relates to novel benzo[b]furan dimers and processes for their preparation. The invention provides a synthetic process for the preparation of benzo[b]furan dimer using mild reaction conditions, which provides a high substituent tolerance and is appropriate for use in solid phase syntheses for producing a library of benzo[b]furan dimers for biological screening.

BACKGROUND OF THE INVENTION

Strategies in new drug discovery often look to natural products for leads in finding new chemical compounds with therapeutic properties. One of the recurring problems in drug discovery is the availability of organic compounds derived from natural sources. Techniques employing combinatorial chemistry attempt to overcome this problem by allowing the high throughput synthesis and testing of hundreds or thousands of related synthetic compounds, called a chemical library. In designing the synthesis of a prospective therapeutic compound or a chemical library, one often looks to natural chemical motifs which are known to have broad biological activity. Benzo[b]furan derivatives are of particular interest due to their frequent occurrence in nature and range of biological activities. Benzo[b]furan is named and numbered according to the Ring Index, American Chemical Society, as follows

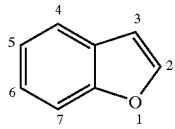

A number of signal transduction pathways are regulated by the binding of a symetrical bivalent ligand which mediates an inducible protein-protein interaction. Chemical inducers of dimerization, or "dimerizers," are a promising new class of compound with a variety of experimental and, potentially, therapeutic applications. Chemically induced dimerization can be used, for example, to activate intracellular signal transduction pathways or to control the activity of a bipartite transcription factor. In some cases the homodimerization of a receptor is sufficient to cause a cellular response. Thus, dimeric small molecules are designed to promote protein-protein interaction. J. F. Amara et al., *Proc. Natl. Acad. Sci.* 1997, 94, 10618; C. T. Rollins, et al., *PNAS* 2000, 97, 7096; V. M. Rivera, *Methods* 1998, 421; and H. E. Blackwell, et al., *Org. Letts.* 2001, 3, 1185.

SUMMARY OF THE INVENTION

The present invention is directed to symmetric benzo[b]furan dimers of the formula I:

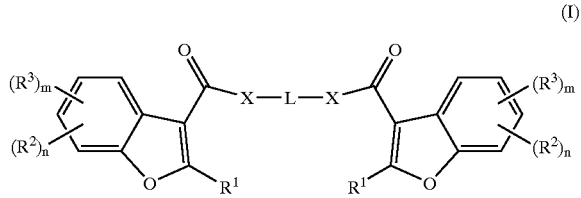

(I)

wherein

L is selected from —(CH$_2$)$_a$—, and a group of the formula

—B-A-B— wherein a is selected from 2–20,

B is —(CH$_2$)$_b$—, —(CH$_2$)$_c$—O—(CH$_2$)$_d$—, or

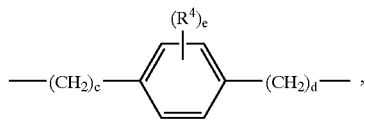

and

A is selected from a group of the formula

—O—, —CH=CH—,

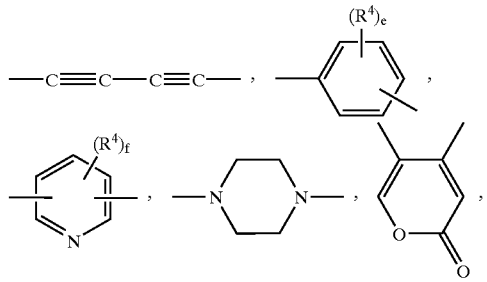

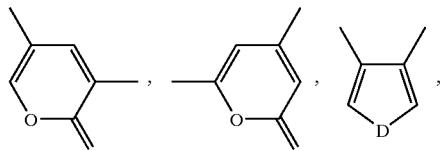

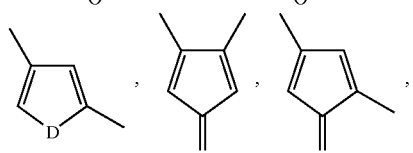

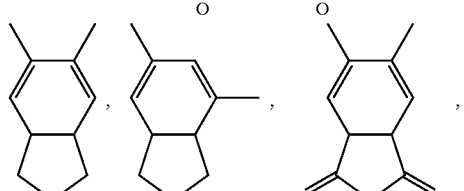

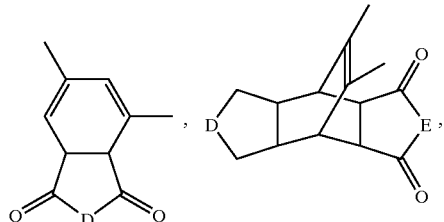

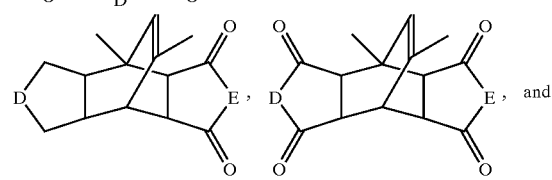

and

-continued

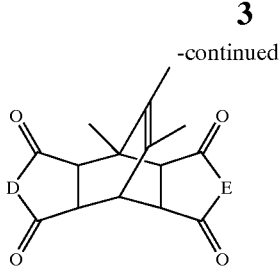

wherein R⁴ is selected from halogen, lower alkyl, lower alkoxy, NO₂, and —NRR,

D and E are independently selected from O, S, Se, CRR and NR, b is selected from 1–10,
c is selected from 1–8,
d is selected from 1–8,
e is selected from 0–4;
f is selected from 0–3, and
R is selected from H, lower alkyl, aralkyl and aryl;

X is selected from O, or —NH—;

R¹ is selected from
   a C₁–C₂₀ alkyl which may be unsubstituted or substituted with one or more substituents selected from CN, halogen, lower alkoxy, thio-lower alkyl, nitro, phosphinos, phosphates, and protected amino;
   a C₁–C₂₀ alkenyl which may be unsubstituted or substituted with one or more substituents selected from CN, halogen, lower alkoxy, thio-lower alkyl, nitro, phosphinos, phosphates, and protected amino;
   an aromatic group which may be unsubstituted or substituted with one or more substituents
      selected from halogen, lower alkyl, lower alkoxy, thio-lower alkyl, nitro, phosphinos, phosphates, and protected amino; and
   an aralkyl which may be unsubstituted or substituted with one or more substituents selected
      from halogen, lower alkyl, lower alkoxy, thio-lower alkyl, nitro, phosphinos, phosphates, and protected amino;

R² is selected from halogen, hydroxy, CN, nitro, lower alkyl, lower alkoxy, thio-lower alkyl, lower alkenyl, cycloalkyl, C₂–C₈ acyl, lower alkyl ester, and lower allyl amide;

R³ is a group of the formula

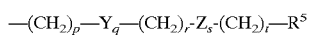

wherein Y and Z are independently selected from O, S, —OCH₂CH₂O—,

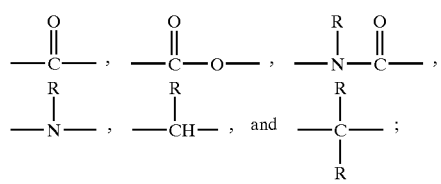

p, r and t are independently selected from values from 0 to 10;

q and s are independently selected from 0 and 1, provided that when t=0 then s=0, and when r=0 then q=0; and R⁵ is selected from OH, CO₂H,

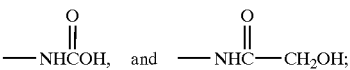

n is selected from 0–4, and m is 0 or 1, with the proviso that the sum of n plus m does not exceed 4.

The invention also provides a synthetic process for the preparation of compounds of the formula I. The process uses mild reaction conditions, which provides a high substituent tolerance. Thus, the process is applicable to the preparation of a wide variety of benzo[b]furan dimers with diverse substitution patterns. Additionally, the process is appropriate for use with the solid-support (solid phase) synthesis of compounds of the formula I. The process provides a method for producing a library of benzo[b]furan dimers for biological screening. Thus, the present invention also relates to a library of benzo[b]furan dimers and a method for producing a library of benzo[b]furan dimers.

DETAILED DESCRIPTION

The term "halo" or "halogen" as used herein includes fluorine, chlorine, bromine and iodine.

The term "lower alkyl" as used herein contemplates both straight and branched chain alkyl radicals containing from one to six carbon atoms and includes methyl, ethyl, propyl, isopropyl, butyl, isobutyl, tert-butyl, and the like.

The term "cycloalkyl" as used herein contemplates cyclic alkyl radicals containing form 3 to 7 carbon atoms and includes cyclopropyl, cyclopentyl, cyclohexyl, and the like.

The term "lower alkenyl" as used herein contemplates both straight and branched chain alkene radicals containing from two to six carbon atoms. Unless otherwise specified herein, the alkene groups disclosed herein may be present as the individual cis or trans isomers or mixtures thereof.

The term "lower alkynyl" as used herein contemplates both straight and branched chain alkyne radicals containing from two to six carbon atoms.

The term "C₂–C₈ acyl" as used herein contemplates both straight and branched chain acyl radicals containing from two to eight carbon atoms and includes acetyl, propionyl, 2-methylbutyryl, and the like.

The term "lower alkyl ester" as used herein contemplates the straight and branched chain lower alkyl esters including —CO₂CH₃, —CO₂CH₂CH₃, —CO₂CH(CH₃)CH₂CH₃, and the like.

The term "lower alkyl amide" as used herein contemplates the straight and branched chain lower alkyl amides including, but not limited to

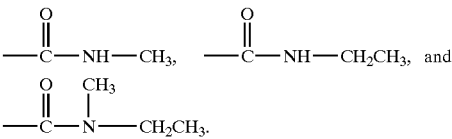

The term "phosphino" as used herein contemplates a phosphine group, wherein the two groups bonded to the phosphorus atom are independently selected from lower alkyl, aryl, C₂–C₈, acyl, and sulfonyl.

The term "phosphate" as used herein contemplates a phosphate group, wherein the two groups bonded to the phosphate oxygens are independently selected from hydrogen, lower alkyl, aryl, and $C_2$–$C_8$ acyl.

The term "protected amino" as used herein contemplates an amino group, wherein one or both groups bonded to the nitrogen atom are independently selected from lower alkyl, aryl, $C_2$–$C_8$ acyl, and sulfonyl.

The terms "aralkyl" as used herein contemplates a lower alkyl group which has as a substituent an aromatic group.

The terms "aromatic group" or "aryl" as used herein contemplates stable 5- and 6-membered single-ring aromatic groups that may include from zero to four heteroatoms, for example, benzene, pyrrole furan, thiophene, imidazole, oxazole, thiazole, triazole, pyrazole, pyridine, pyrazine, pyridazine and pyrimidine, and the like. Those aromatic groups having heteroatoms in the ring structure may also be referred to as "aryl heterocycles" or "heteroaromatics". The terma "aromatic group" or "aryl" also includes polycyclic ring systems having two or more rings in which two carbons are common to two adjoining rings (the rings are "fused") wherein at least one of the rings is aromatic, e.g., the other rings can be cycloalkyls, cycloalkenyls, aryl, heterocycles and/or heteroaryls.

All value ranges, for example those given for n and m, are inclusive over the entire range. Thus, a range between 0–4 would include the values 0, 1, 2, 3 and 4.

Benzo[b]furan Dimers

The invention provides novel symmetric benzo[b]furan dimers and a process for their preparation. The benzo[b]furan dimers of the present invention are compounds of the formula I:

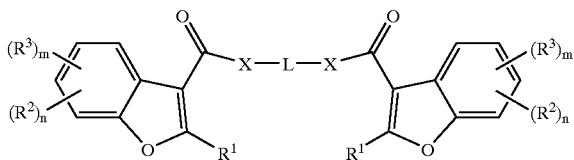

wherein

L is selected from —$(CH_2)_a$—, and a group of the formula

—B-A-B— wherein a is selected from 2–20,

B is —$(CH_2)_b$—, —$(CH_2)_c$—O—$(CH_2)_d$—, or

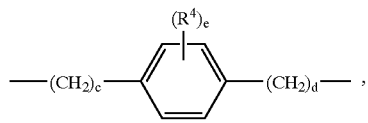

and

A is selected from a group of the formula

—O—, —CH=CH—,

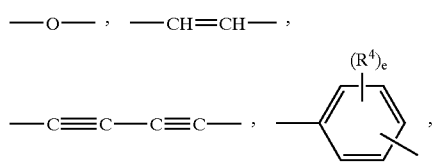

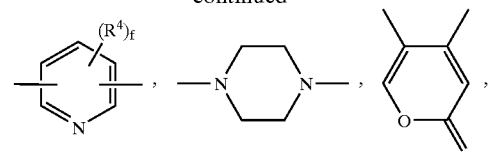

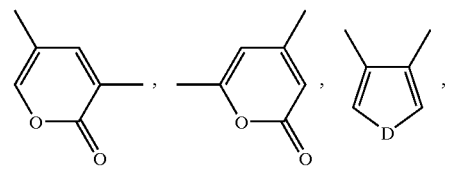

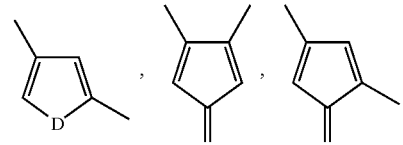

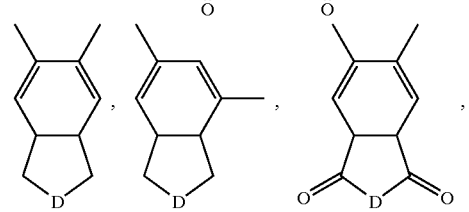

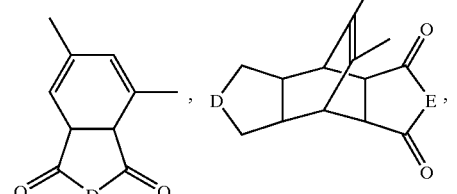

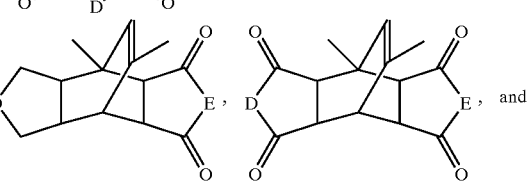

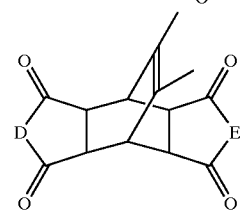

wherein $R^4$ is selected from halogen, lower alkyl, lower alkoxy, $NO_2$, and —NRR, D and E are independently selected from O, S, Se, CRR and NR, b is selected from 1–10,
c is selected from 1–8,
d is selected from 1–8,
e is selected from 0–4;
f is selected from 0–3, and
R is selected from H, lower alkyl, aralkyl and aryl;

X is selected from O, or —NH—;

$R^1$ is selected from a $C_1$–$C_{20}$ alkyl which may be unsubstituted or substituted with one or more substituents selected from CN, halogen, lower alkoxy, thio-lower alkyl, nitro, phosphinos, phosphates, and protected amino;

a $C_1$–$C_{20}$ alkenyl which may be unsubstituted or substituted with one or more substituents selected from CN, halogen, lower alkoxy, thio-lower alkyl, nitro, phosphinos, phosphates, and protected amino;

an aromatic group which may be unsubstituted or substituted with one or more substituents
   selected from halogen, lower alkyl, lower alkoxy, thio-lower alkyl, nitro, phosphinos, phosphates, and protected amino; and an aralkyl which may be unsubstituted or substituted with one or more substituents selected
   from halogen, lower alkyl, lower alkoxy, thio-lower alkyl, nitro, phosphinos, phosphates, and protected amino;

$R^2$ is selected from halogen, hydroxy, CN, nitro, lower alkyl, lower alkoxy, thio-lower alkyl, lower alkenyl, cycloalkyl, $C_2$–$C_8$, acyl, lower alkyl ester, and lower alkyl amide;

$R^3$ is a group of the formula

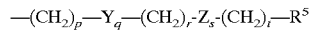

wherein Y and Z are independently selected from O, S, —OCH$_2$CH$_2$O—,

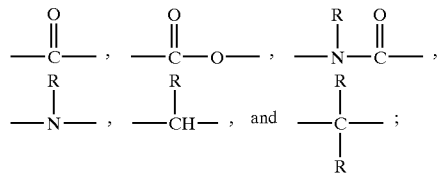

p, r and t are independently selected from values from 0 to 10;

q and s are independently selected from 0 and 1, provided that when t=0 then s=0, and when r=0 then q=0; and $R^5$ is selected from OH, CO$_2$H,

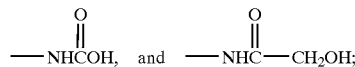

n is selected from 0–4, and m is 0 or 1, with the proviso that the sum of n plus m does not exceed 4.

When Y or Z are ester and amide functionalities,

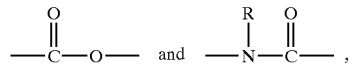

the group may be in either available orientation. Thus, for example, when Y is

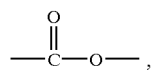

then $R^3$ may be chosen from

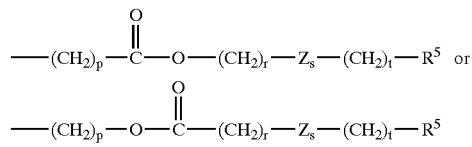

When one or more chiral centers are present in the compounds of the present invention, the individual isomers and mixtures thereof (e.g., racemates, etc.) are intended to be encompassed by the formulae depicted herein.

In a preferred embodiment of the invention, A is selected from a group of the formula

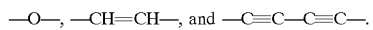

Preparing the Compounds of Formula I

The invention also provides a synthetic process for the preparation of compounds of the formula I. The inventive process uses mild reaction conditions, which provides a high substituent tolerance. The product is obtained in high yield and high purity. The process of the present invention, summarized in Scheme I below, comprises the steps of (a) Sonogashira Reaction, (b) carbonylative annulation, and (c) coupling:

Scheme I (a) Sonogashira Reaction:

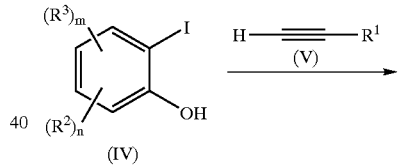

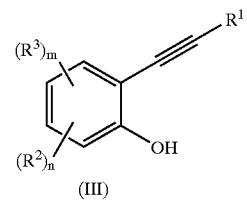

(b) carbonylative annulation:

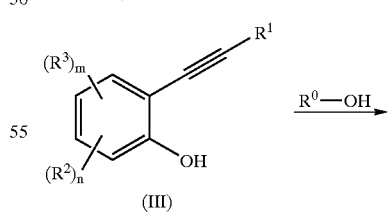

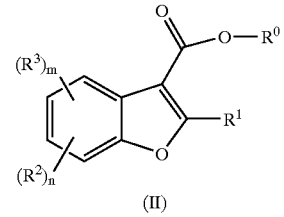

(c) coupling

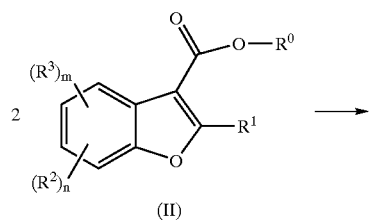

(II)

→

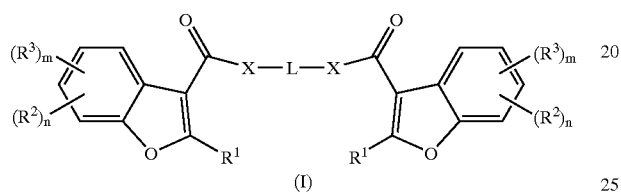

(I)

wherein $R^1$, $R^2$, $R^3$, X, L, n and m are as described above for a compound of the formula I, and $R^0$ is lower alkyl, aralkyl, or aryl, wherein the lower alkyl, aralkyl, or aryl, may optionally substituted with one or more halogen, CN and nitro, or $R^0$ is selected from a group of the formula —L—OH, and —B-A', wherein A and B are as described above for a compound of the formula I, and A' is —CH=$CH_2$ or —C≡CH.

Each step is performed under mild reaction conditions, giving the overall process a high substituent tolerance. The synthetic process is useful in the solution phase preparation of compounds of the formula I. Additionally the synthetic process is appropriate for use with the solid-support (solid phase) synthesis of compounds of the formula I. Thus, the process provides a method for producing a library of benzo[b]furan dimers for biological screening.

Sonogashira Reaction

Using a Sonogashira reaction, a compound of the formula III

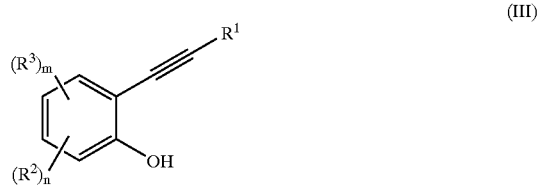

(III)

is prepared by reacting a compound of the formula IV

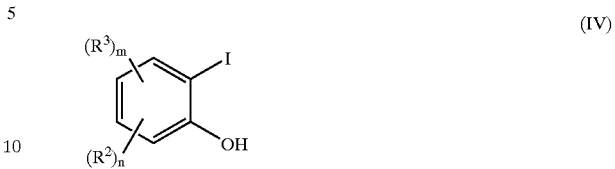

(IV)

with a terminal alkyne represented by the formula V:

(V)

in the presence of base and a transition metal catalyst, wherein $R^1$, $R^2$, $R^3$, n and m are as described above for the compound of the formula I. A suitable base may be, for example, an organic base such as a primary, secondary or tertiary amine. Non-limiting examples include triethylamine, diisopropylamine, 1,8-diazabicyclo-[5.4.0]-undec-7-ene (DBU), 1,5-diazabicyclo-[4,3,0]-non-5-ene (DBN), or 1,4-diazabicyclo-[2.2.2]-octane (DABCO). Alternatively, an inorganic base may be used, such as an alkali metal or alkaline earth metal salt, such as a carbonate, bicarbonate or acetate salt.

The metal catalyst may be in the form of a salt or a complex with organic ligands. Particularly suitable metal catalysts are, for example, the Group VIII metals, preferably Pd(0) complexes or a Pd(II) salt. The ligands may be selected from, for example, phosphorus-containing ligands, such as triphenylphosphine ($PPh_3$) and 1,2-bis(diphenylphosphino)ethane (dppe). Preferred palladium catalysts include $Pd(PPh_3)_2Cl_2$, $Pd(PPh_3)_4$ and $Pd(OAc)_2$. The reaction is performed in the presence of a Cu(I) salt, such as a Cu(I) halide, $Cu_2O$, and CuCN, preferably CuI or CuCl. Suitable organic solvents include, but are not limited to, dioxane, tetrahydrofuran (THF) dimethylformamide (DMF), acetonitrile, dimethylsulfoxide, and other polar aprotic solvents or mixtures thereof. For further discussion of the Sonogashira reaction, see Sonogashira, K.; Tohda, Y,; Hagihara, N. *Tetrahedron Lett.* 1975, 4467–4470; Sonogashira, K. In *Comprehesive Organic Synthesis*, Trost, B. M.; Fleming, L., Eds., Pergamon Press: New York, 1991, Vol. 3, chapter 2.4; Liao, Y.; Fathi, R.; Reitman, M.; Zhang, Y.; Yang, Z. *Tetrahedron Lett.* 2001, 42, 1815–1818; Nicolaou, K. C.; Smith, A. L. *Acc. Chem. Res.* 1992, 25, 497–503; Porco, J. A., Jr.; Schoenen, F. J.; Stout, T. J.; Clardy, J.; Schreiber, S. L. *J. Am. Chem. Soc.* 1990, 112, 7410–7411; Hundertmark, T.; Littke, A. F.; Buchwald, S. L.; Fu, G. C. *Org. Lett.* 2000, 2, 1729–1731, and references therein; Takeuchi, R.; Tanabe, K.; Tanaka, S. *J. Org. Chem.* 2000, 65, 1558–1561; Arterbum, J. B.; Rao, K. V.; Perry, M. C. *Tetrahedron Lett.* 2000, 41, 839–842; Gan, Z.; Roy, R.

Tetrahedron Lett. 2000, 41, 1155–1159; Godt, A.; Unsal, O.; Roos, M. J. Org. Chem. 2000, 65, 2837–2842; Wu, M. J.; Lin, C. F.; Chen, S. H. Org. Lett. 1999, 1, 767–768; Yoshimura, F.; Kawata, S.; Hirama, M. Tetrahedron Lett. 1999, 40, 8281–8286; Ma, S.; Shi, Z.; Yu, Z. Tetrahedron Lett. 1999, 40, 2393–2396; Tretyakov, E. V.; Knight, D. W.; Vasilevsky, S. F. J. Chem. Soc., Perkin Trans. 1, 1999, 3713–3720; Thorand, S.; Krause, N. J. Org. Chem. 1998, 63, 8551–8553; and Sonogashira, K. in *Metal-Catalyzed Cross-Coupling Reactions*; Diederich, F., Stang, P. J., Wiley-VCH: New York, 1998; Chapter 5, each of which is incorporated by reference.

Carbonylative Annulation

A benzo[b]furan monomer of the formula (II)

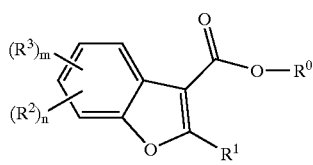

is prepared by treating a compound of the formula III with an alcohol of the formula $R^0$—OH in the presence of a transition metal catalyst, carbon monoxide and a base, wherein $R^1$, $R^2$, $R^3$, n and m are as described above for the compound of the formula I, and $R^0$ is lower alkyl, aralkyl, or aryl, wherein the lower alkyl, aralkyl, or aryl, may optionally substituted with one or more halogen, CN and nitro, or $R^0$ is selected from a group of the formula -L-OH, and —B-A', wherein L and B are as described above for a compound of the formula I, and A' is —CH=$CH_2$ or —C≡CH.

The transition metal catalyst is preferably a palladium(II) compound, such as $Pd(PPh_3)_2Cl_2$, $Pd(PPh_3)_4$, $Pd(OAc)_2$, $PdCl_2$, $PdI_2$, $PdI_2$-thiourea, $Pd(CH_3CN)_2$, and $Pd(bpy)Cl_2$. A particularly preferred catalyst is $Pd(PPh_3)_2Cl_2$ in the presence of a ligand such as dppp, 2,2'-dipyridyl (bpy), 2-$PyPPh_2$, thiourea, $CBr_4$, and p-methylphenylsulfonyl. Preferred bases include, but are not limited to, metal salts, such as alkali metal acetates, carbonates, and phosphates. A particularly preferred base in CsOAc. Suitable organic solvents include THF, $CH_3CN$, benzene, toluene, dioxane and polar aprotic sovents such as DMF. A particularly preferred solvent is DMF. The carbonalative annulation preferrably is performed at a temperature of about 45° C. to about 100° C.

The ester product (II) may be used in the following coupling step directly or after additional chemical modification. In one embodiment, the ester group is cleaved by saponification or other method known in the art to give the corresponding carboxylic acid, $II_b$ (for a review of ester cleavage reactions see Greene, T. W.; Wuts, P. G. M. *Protective Groups in Organic Synthesis*, 2$^{nd}$ ed.; (Wiley: New York, 1991), pages 229–270, particularly pages 229–231, and the references contained therein). As would be apparent to a person of ordinary skill in the art, the method for cleavage of the ester should be compatible with the other substituents and with the solid support and linker (for a solid phase synthesis). The resulting carboxylic acid, $II_b$

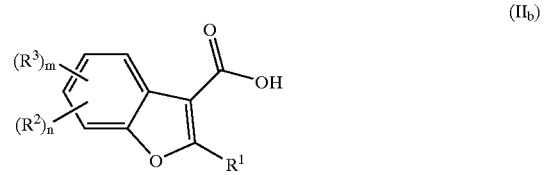

can be activated for further reaction by a method known in the art, for example, as an acid halide or anhydride, or through the use of dehydrating agents, such as DCC.

Alternatively, an active ester may be introduced directly into the compound of the formula II by selection of an appropriate alcohol, $R^0$—OH, for use in the carbonylative annulation. A preferred active ester is derived from the alcohol HO—$CH_2$—$CF_3$ ($R^0$=$CH_2$—$CF_3$). The term "active ester" as used herein contemplates esters that are readily susceptible to nucleophillic substitution, for example, by transesterification.

Coupling

In a further synthetic step, two benzo[b]furan monomers are coupled to give a benzo[b]furan dimer of the formula I. The coupling can be performed as a single reaction step or as two or more consecutive steps, depending on the nature of the benzo[b]furan monomer being coupled.

In one embodiment, the compound of the formula II comprises a terminal olefin. The resulting compound can be represented by the formula $II_c$

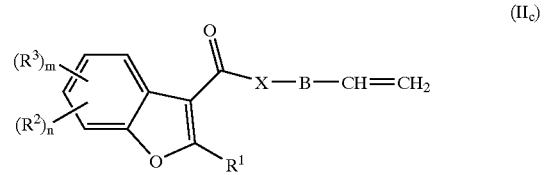

wherein $R^1$, $R^2$, $R^3$, X, B, n and m are as defined above for a compound of Formula I. The presence of terminal olefin allows the coupling of two molecules of the formula $II_c$ using olefin metathesis. Grubbs, R. H. Chang, S., *Tetrahedron* 1998, 54, 4413–4450; Furstner, A. *Angew. Chem., Int. Ed.* 2000, 39, 3012–3–43; Blackwell, H. E.; O'Leary, D. J.; Chatterjee, A. K.; Washenfelder, R. A.; Bussman, D. A.; Grubbs, R. H. *J. Am. Chem. Soc.* 2000, 122, 58–71, and references therein. The olefin metathesis reaction couples two molecules of the formula $II_c$ in the presence of a ruthenium catalyst to give a benzo[b]furan dimer of the formula I, wherein A is —CH=CH—, represented below as formula $I_c$

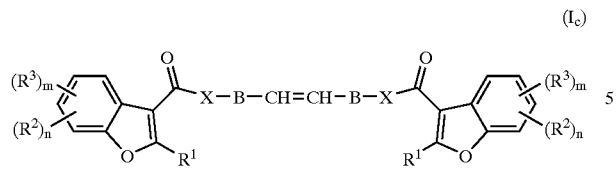

(I_c)

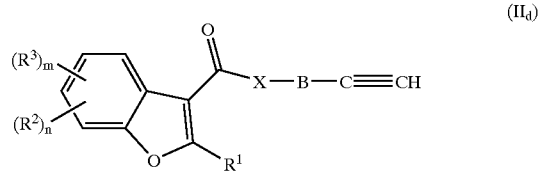

(II_d)

wherein $R^1$, $R^2$, $R^3$, X, B, n and m are as defined above for a compound of Formula I.

The preferred catalyst for the olefin metathesis is Grubb's catalyst, Bis(tricyclohexylphosphine)benzylidine ruthenium (IV) dichloride, $(RUCl_2(CHC_6H_5)[P(C_6H_{11})_3]_2)$. Other catalysts include bis(tricyclohexylphosphine)3-methyl-2-butenylidene ruthenium (IV) dichloride $(RuCl_2(C_5H_8)[P(C_6H_{11})_3]_2)$, and tricyclohexylphosphine[1,3-bis(2,4,6-trimethylphenyl)-4,5-dihydroimidazol-2-ylidene] [benzylidine]ruthenium (IV) dichloride $(RuCl_2[C_{21}H_{26}N_2][CHC_6H_5]P(C_6H_{11})_3)$. Suitable organic solvents include, but are not limited to, methylene chloride, THF, dioxane, $CH_3CN$, and toluene. The preferred solvent is methylene chloride. The olefin metathesis should be carried out under an inert atmosphere with dried solvents.

In another embodiment, the compound of the formula II comprises a terminal alkyne. The resulting compound can be represented by the formula $II^d$ wherein $R^1$, $R^2$, $R^3$, X, B, n and m are as defined above for a compound of Formula I. The presence of a terminal alkyne allows coupling of two molecules of the formula $II_d$ in the presence of a transition metal catalyst. Preferered reaction conditions include: providing the acetylenes (1 equiv.), a Cu(I) salt (0.05 equiv.), such as CuI, CuCl, CuOAc, CuBr or $CuNO_3$, a Cu(II) salt (2 equiv.) such as $CuCl_2$, $CuBr_2$, $CuI_2$, $Cu(NO_3)_2$ or $Cu(OAc)_2$, a Ag(I) sal (2.5 equiv.) such as AgOAc, $Ag_2SO_4$, AgOTf, $AgNO_3$, AgOTs or $AgClO_4$, and excess base (20 equiv.) such as 2,6-lutidine, N,N,N,N-Tetramethylethylenediamine, pyridine, DABCO or DBU in an appropriate organic solvent. Particularly preferred conditions for acetylene coupling include $CuI/CuCl_2$, N,N,N',N'-tetramethyl-1,2-ethanediamine (TMEDA), and DBU in methylene chloride. The coupling of the compound of formula $II_d$ will give a benzo[b]furan dimer wherein A is —C≡C—C≡C—:

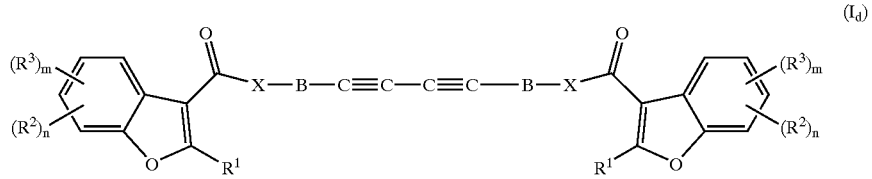

(I_d)

wherein $R^1$, $R^2$, $R^3$, X, B, n and m are as defined above for a compound of Formula I.

Alternatively, the compound of the formula $II_d$ may be coupled in the presence of an transition metal catalyst to give a cyclic organometallic intermediate, as depicted below:

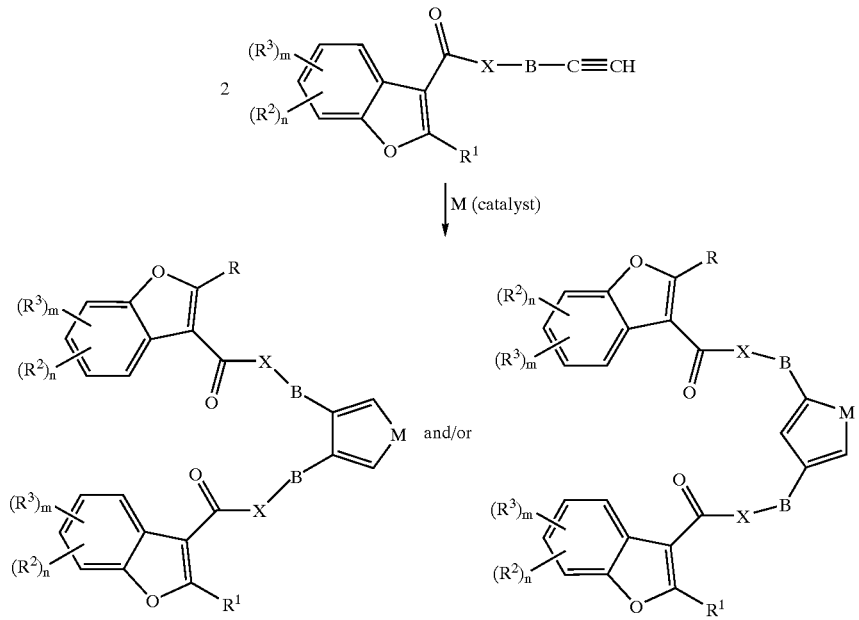

The cyclic organometallic intermediate is useful in the formation of a variety of linking structures, including substituted cyclohex-di-enes with fused heterocycles (1, 1', 2 and 2') and their Diels-Alder cycloaddition products (3–4), substituted heterocycles (7–13), cyclopenta-2,4-dienones (14–15) and substituted benzenes (16–18), as shown in the following scheme:
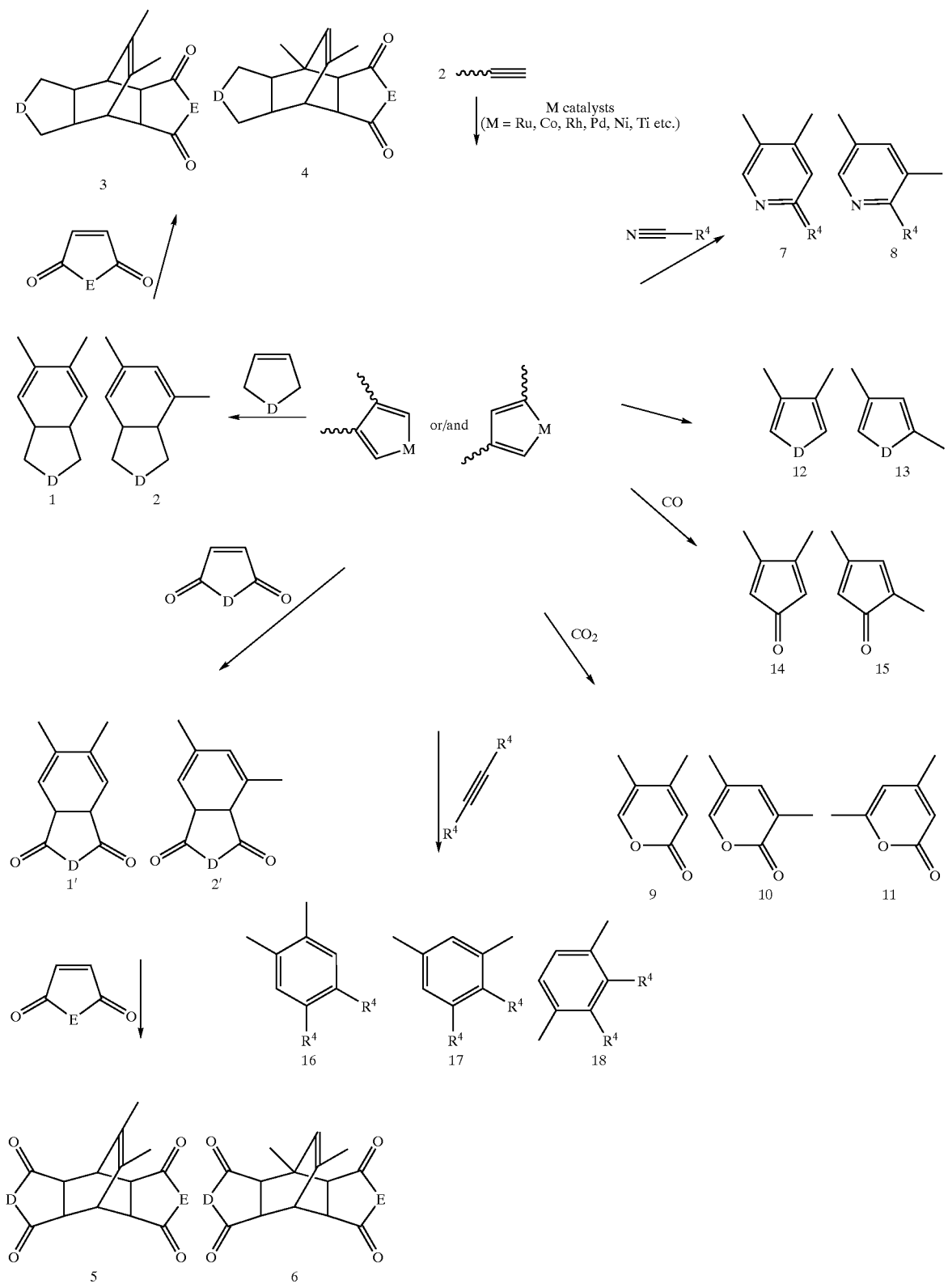

wherein the terminal alkyne of the formula $II_d$ is represented schematically as 

and D, E, and $R^4$ are as described above for the compound of Formula I.

In another embodiment, the compound of the formula II comprises an active ester. The active ester may be introduced directly into the compound of the formula II by selection of an appropriate alcohol, $R^0$—OH, for use in the carbonylative annulation. A preferred active ester is derived from the alcohol HO—$CH_2$—$CF_3$ ($R^0$=$CH_2$—$CF_3$). Two molecules of the active ester are coupled by reaction with a difunctional alcohol or amine of the formula

HX-L-XH wherein, X and L are as defined above for compound of the formula I, to give a compound of the formula I. Alternatively, the acid $II_b$, or a corresponding activated acid, is coupled by reaction with a difunctional alcohol or amine. The caboxylic acid $II_b$ may be activated in situ using a dehydrating agent known in the art, such as DCC. In either case, the difunctional alcohol or amine is combined with at least two equivalents of the activated 3-benzofuran carboxylate in a suitable organic solvent.

In another embodiment, the steps of carbonylative annulation and coupling are performed concurrently in a single step. In this embodiment, the carbonylative annulation of a compound of the formula III is performed in the presence of a difunctional alcohol, HO-L- OH ($R^0$ is -L-OH) to give a compound of the formula I:

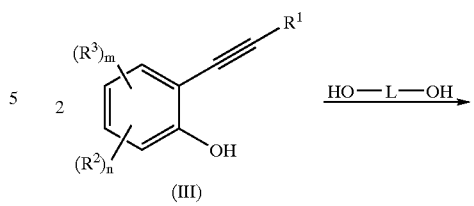

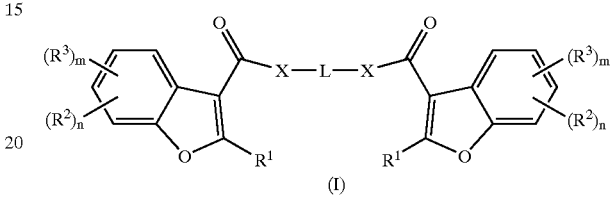

In one embodiment, the process of the invention is adapted for use as a solid phase synthesis. In a solid phase synthesis the reactions are carried out on macroscopic particles (as known as the solid support, or resin) made of material that is insoluble in the reaction mixture, to which one of the reactants is bound. A compound of the formula IV linked to a solid support, represented by the formula $IV_a$, is treated according to the process of reaction Scheme I. The product represented by the formula $I_a$, is cleaved from the solid support. This embodiment is summarized in reaction Scheme II:

Scheme II

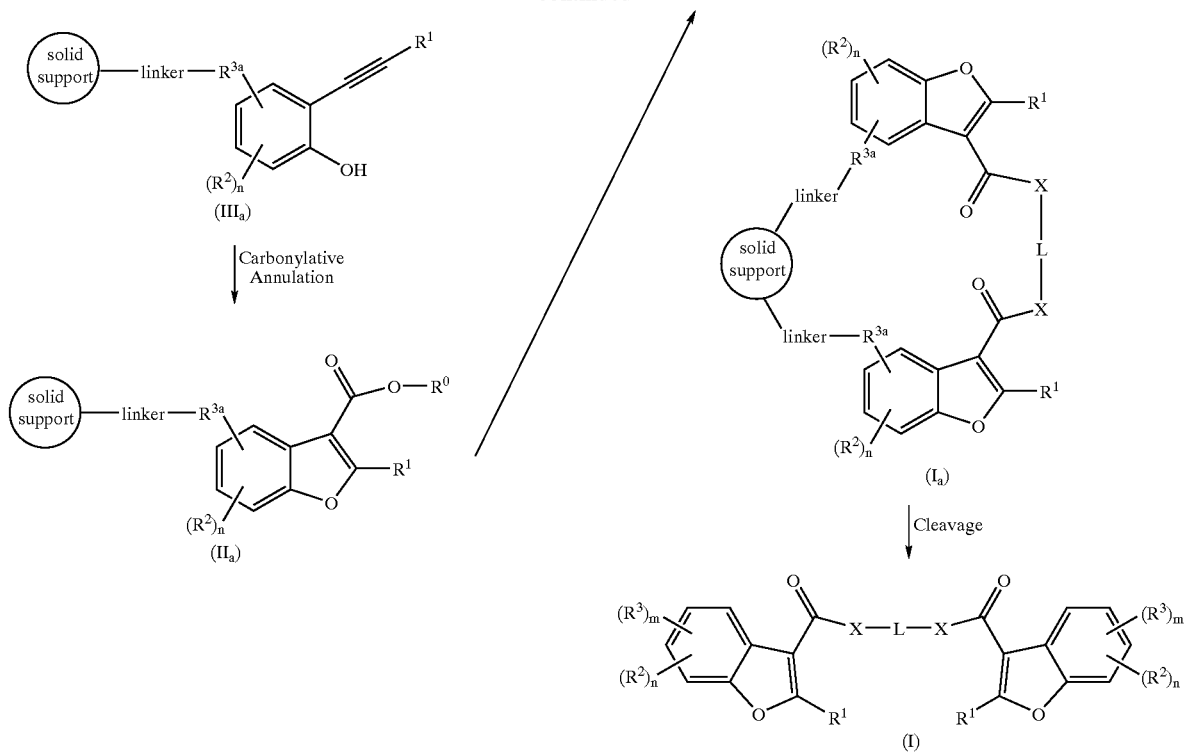

wherein $R^1$, $R^2$, $R^3$, X, L, and n are as described above for a compound of the formula I, and $R^0$ is as described above for a compound of the formula II. $R^{3a}$ is selected from a group of the formula

wherein Y and Z are independently selected from O, S, —OCH$_2$CH$_2$O—,

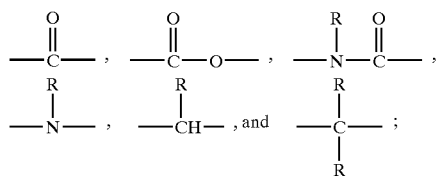

p, r and t are independently selected from values from 0 to 10;

q and s are independently selected from 0 and 1, provided that when t=0 then s=0, and when r=0 then q=0;

R is selected from H and lower alkyl; and $R^{5a}$ is selected from —O—, —CO$_2$—,

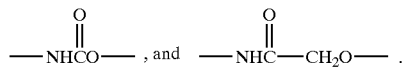

$R^3$ is the chemical group that results from the cleavage of $R^{3a}$ and linker. Thus, for example, if $R^{3a}$ is O, then $R^3$ may be HO— after cleavage, and if $R^{3a}$ is —O—CH$_2$CH$_2$—, then $R^3$ may be HO—CH$_2$CH$_2$— after cleavage. More generally, when $R^{3a}$ is selected from a group of the formula —(CH$_2$)$_p$—Y$_q$—(CH$_2$)$_r$-Z$_s$-(CH$_2$)$_t$—R$^{5a}$, then $R^3$ may be a group of the formula —(CH$_2$)$_p$—Y$_q$—(CH$_2$)$_r$-Z$_s$-(CH$_2$)$_t$—R$^{5a}$H, wherein Y, Z, q, r, s, and t are the same between $R^3$ and $R^{3a}$.

The solid support is an insoluble, functionalized, polymeric material to which library members or reagents may be attached via a linker, allowing them to be readily separated (by filtration, centrifugation, etc.) from excess reagents, soluble reaction by-products, or solvents. The solid support is chosen from the solid support materials known in the art, e.g., commercially available resins used for solid phase synthesis in combinatorial chemistry or in solid phase peptide synthesis. For example, the solid support may be chosen from cross-linked polystyrene resins, polystyrene/DVB-polyethylene resins (for example, TentaGel resin, ArgoGel, etc.), controlled-pore glass and Kieselguhr/polyacrylamide. A preferred solid support is a high-capacity polystyrene macrobead.

The linker is a chemical moiety that provides a means of attachment for the immobilized chemical reagent to the solid support. The linker may be any chemical component capable of being selectively cleaved to release a compound of the formula I from the solid support. Yields for the loading and cleavage to the linker should be as quantitative as possible. The linker may be chosen from those customarily used in the art that are stable to the reactions conditions. Examples of suitable linkers may be found in the review by Guillier et al., Chem. Rev. 2000, 100, 2019–2157. Preferred linkers are silyl based linkers, for example the silyl based linkers disclosed in Sternson et al., J. Am. Chem. Soc. 2001, 123, 1740–1747, Blackwell et al., Org. Lett. 2001, 3, 1185–1188, Pelish et al., J. Am. Chem. Soc. 2001, 123, 6740–6741, and Tallarico et al., J. Comb. Chem. 2001, 3, 312–318, and the like.

As would be recognized by one of ordinary skill in the art, it may be advantageous to employ a temporary protecting group in achieving the final product. The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; (Wiley: New York, 1991)).

EXAMPLES

Introductory Materials

In the illustrative examples set forth herein, the following general methods, apparatus and material may be employed.

Materials: Reaction solvents were commercially purchased from Acros and Aldrich without further purification and reagents were used as received. Reactions for the synthesis of the starting material were monitored by thin-layer chromatography (TLC) on 0.25 mm precoated Merck Silica Gel 60 $F_{254}$, visualizing with ultraviolet light or phosphomolybdic acid stain. Flash column chromatography was performed on Merck Silica Gel 60 (230–400 mesh) using reagent grade hexanes, dichloromethane, methanol and ethyl acetate.

Solid Phase Reactions:

Reaction Apparatus: Small-scale solid phase reactions (1–20 mg resin) were performed in 1 or 2 mL of polypropylene Fisherbrand® flat top microcentrifuge tubes (Fisher Scientific 05-408-25A) or 1 or 2 mL of fritted polypropylene Bio-Spine® chromatography columns (Bio-Ras 732–6008) with 3600 rotation on a Barnstead-Thermilyne Labquake™ Shaker (VWR 56264-306) or a Genie 2™ Fisher Vortex (cat. 12–812). Medium-scale solid phase reactions (20–200 mg resin) were performed in 5 or 10 mL fritted polypropylene chromatography columns PD-10 (Amersham Pharmacia Biotech AB 17-0435-01) and large-scale solid phase reactions (>200 mg resin) were performed in 25–250 mL fritted glass tubes equipped for vacuum filtration and $N_2$ bubbling with 360° rotation on a Glas-Col® tissue culture rotator (VWR. 62404-006). Test library synthesis was carried out in NanoKanTM microreactors, and all radiofrequency encoding/sorting equipment utilized herein is available from IRORI, a Discovery Partners International Company (San Diego, Calif.).

Washing Apparatus and procedure: The washing was carried out on a Vac-Mano® Laboratory Vacuum Manifold (Promega A7231) with 2-way Teflon stopcocks. The following standard wash procedure was used in sequence: $CH_2Cl_2$, DMF, MeOH, DMF, $CH_2Cl_2$ (each for 1–2 h).

Standard Cleavage and drying procedure: The resins (10–20 beads) were suspended in THF (0.2 mL), and HF/Pyridine (0.01 mL) was added. The mixture was shaken for 1 h, then methoxytrimethylsilane ((trimetylsilyl) methanol) (TMSOMe) (0.02 mL) was added and the mixture was further shaken for another 5 min. Most of solvents and reagents were removed in a GeneVac VC3000D vapor condenser (IPSWICH England) for 30 min. and further dried in Dura-Dry™ Freeze-dryer at <50 mT overnight or for 1–3 days.

Analysis: High-resolution mass spectra were performed at Harvard University Mass Spectrometry (JEOL SX-102A and AX-505H Magnetic Sector). $^1H$ and $^{13}C$ NMR spectra were recorded on a Varian Unity INPVA 500 MHz spectrometer and are referenced to residual solvents peaks (CDCl$_3$: $^1H$: δ 7.27 ppm, $^{13}C$: δ 77.23 ppm; DMSO-d$_6$: $^1H$: δ 2.50 ppm (DMSO-d$_6$), $^{13}C$: δ 39.51 ppm; CD$_2$Cl$_2$: $^1H$: δ 5.20 ppm). $^1H$-$^1H$ couplings are assumed to be first order, and peak multiplicity is reported as a s (single), d (doublet), t (triplet), q (quartet), m (multiplet), or b (broad). In regard the products cleaved from the beads (10–20 macrobeads), their $^1H$ NMR spectra were recorded with 8–20 scans. All LC-MS spectra were obtained on a Micromass Platform LCZ mass spectrometer in atmospheric pressure chemical ionization (AP-CI) mode or electro spray ionization (ESI) attached to a Waters 2690 HPLC system (Separations Module, AllianceTM). LC-MS chromatography was performed on a Waters Symmetry C18 Column (3.5 μm, 2.1×50 mm, W93491F 26) using a flow rate of 0.4 mL/min in a gradient of 15–100% $CH_3CN$ in $H_2O$ in 10 min with 2 min wash. Column temperature: 30° C. [APCI$^+$ or ES$^+$] scan 120–1200 CV 35V, [APCI$^-$ or ES$^-$] scan 120–1200 CV 25V. injection Volume: 5 μl. Software: Masslynx. Normally, product cleaved from one bead is sufficient for LC-MS analysis. After the product was dried completely, it was dissolved in 0.05 mL THF, MeOH or $CH_3CN$ (HPLC grade) and ready for LC-MS test, which was reported as: LC-MS (retention time, [M+1]$^+$. (APCI$^+$ or ES$^+$) or [M–1]$^+$. (APCI$^-$ or ES$^-$)).

Example 1

General Procedure for Synthesis of the Starting Materials in Solution

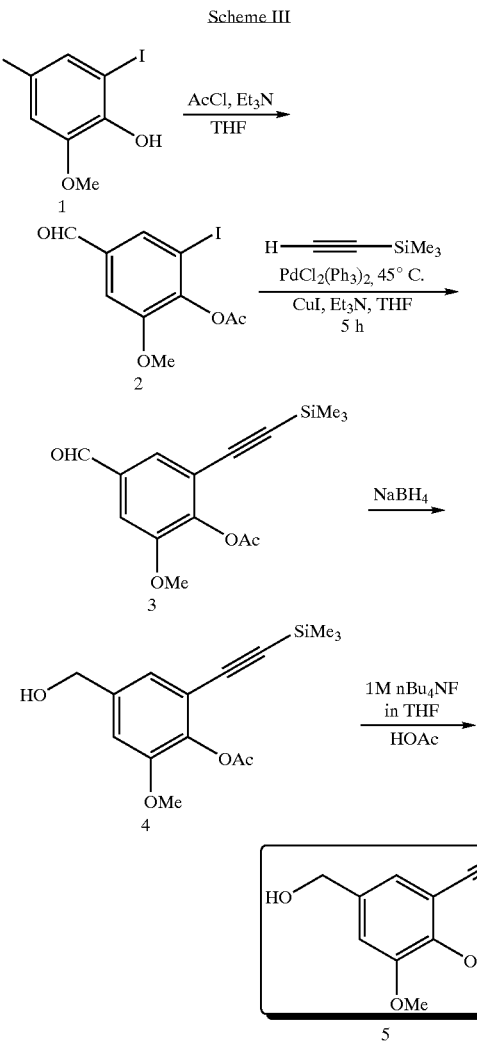

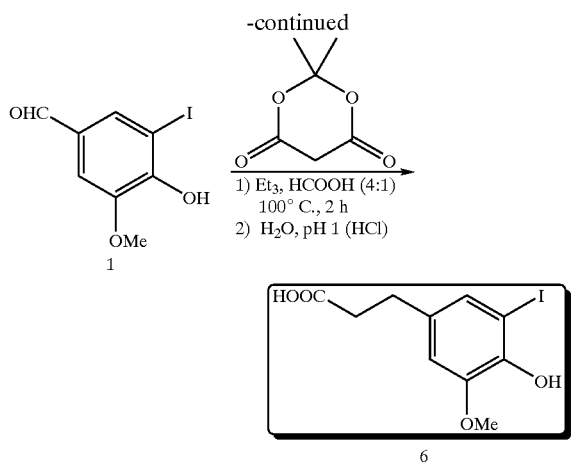

4-Acetoxy-3-methoxy-5-4-acetoxy-3-iodo-5-methoxybenzadehyde (2):

5-Iodovanillin 1 (10.0 g, 36 mmol) was dissolved in dry THF (100 mL) and dry Et$_3$N (25 mL), then cooled to 0° C. AcCl (10 mL, excess) was added slowly, and the cold bath was removed after addition, and then the reaction mixture was stirred under Ar over night. The reaction mixture was mixed with ethyl acetate (200 mL), then washed with a saturated aqueous solution of NH$_4$Cl (2×20 mL), and the organic layer was dried (Na$_2$SO$_4$). The solvent was removed under vacuum and the residue was purified by flash chromatography (ethyl acetate/hexane 1:10) to give compound 2 (Rf=0.5, ethyl acetate/hexane 1:5) as a white solid (11.0 g, 96%). mp: 106–107° C. $^1$H NMR (500 MHz, CDCl$_3$): δ 9.88 (s, 1H), 7.88 (s, 1H), 7.45 (s, 1H), 3.90 (s, 3H), 2.40 (s, 3H).

[(Trimethylsilyl)ethynyl]benzaldehyde (3):

Compound 2 (44.8 g, 0.14 mol), trimethylsilyl acetylene (17.6 g, 0.18 mol), bis(triphenylphosphine)palladium dichloride (1.1 g, 1.5 mmol), CuI (0.58 g, 3.0 mmol) and Et$_3$N (100 mL) were mixed in 1,4-dioxane (100 mL) and the mixture was heated to 45° C. for 6 h. The reaction mixture was mixed with ethyl acetate (300 mL), and was washed with a saturated aqueous solution of NH$_4$Cl (2×50 mL), then the organic layer was dried over Na$_2$SO$_4$. The solvent was removed under a vacuum and the residue was purified by flash chromatography (ethyl acetate/hexane 1:10) to give compound 3 (Rf=0.7, ethyl acetate/hexane=1:5) as a yellowish solid (38.2 g, 94%). $^1$H NMR (500 MHz, CDCl$_3$): δ 9.91 (s, 1H), 7.60 (d, 1H, J=1.5 Hz), 7.46 (d, 1H, J=1.5 Hz), 3.91 (s, 3H), 2.38 (s, 3H), 0.27 (s, 9H).

4-Acetoxy-3-methoxy-5-[(trimethylsilyl)ethynyl] benzenemethanol (4):

Compound 3 (16.0 g, 50 mmol) was dissolved in methanol (150 mL) in a 1 L round bottom flask, and sodium borohydride (5.7 g, 150 mmol) was added in 5 min with vigorously stirring, followed by stirring for another 30 seconds. After addition of acetic acid (15.0 mL) with vigorously stirring in 5 min, a saturated aqueous solution of NH$_4$Cl (150 mL) was added. The methanol in the mixture was removed under a vacuum and the residue was extracted with ethyl acetate (4×50 mL), then the organic layer was dried over Na$_2$SO$_4$. The solvent was removed under vacuum and the residue was purified by flash chromatography (ethyl acetate/hexane=1:1) to give compound 4 (Rf=0.52, ethyl acetate/hexane 1:1) as a yellowish solid (14.9 g, 93%). $^1$H NMR (500 MHz, CDCl$_3$): δ 7.06 (d, 1H, J=1.5 Hz), 6.99 (d, 1H, J=1.5 Hz), 4.64 (s, 2H), 3.84 (s, 3H), 2.34(s, 3H), 0.24 (s, 9H). $^{13}$C NMR (500 MHz, CDCl$_3$): δ168.56, 151.76, 140.67, 139.62, 139.56, 122.69, 118.45, 111.52, 99.81, 99.46, 64.80, 56.27, 20.67, 0.06.

5-Acetoxy-3-ethynyl-4-methoxybenzenemethanol (5):

Compound 4 (10 g, 34 mmol) was dissolved in THF (100 mL), then acetic acid (4.0 mL, 70 mmol) and tributylammoniumfloride (1.0 M in THF) (51 mL, 51 mmol) were added at room temperature. After stirring for 40 min at the same temperature, a saturated aqueous solution of NH$_4$Cl (50 mL) was added, followed by extraction with ethyl acetate (3×60 mL), and the combined extracts was dried (Na$_2$SO$_4$). The solvent was removed under a vacuum, and the residue was purified by flash chromatography (dichloromethane) to give 5 (Rf=0.5, ethyl acetate/hexane 1:1) as a yellowish liquid (6.8 g, 90%). $^1$H NMR (500 MHz, CDCl$_3$): δ 7.11 (s, 1H), 7.05 (s, 1H), 4.68 (s, 2H), 3.87 (s, 3H), 3.23 (s, 1 H), 2.38(s, 3H). $^{13}$C NMR (500 MHz, CDCl3): δ 168.85, 151.75, 140.85, 139.92, 122.99, 117.37, 111.86, 82.08, 78.54, 64.66, 56.31, 20.75.

3-[4-Hydroxy-3-iodo-5-methoxyphenyl]propionic acid (6): see EP 0578850 A1, p7. Compound 6 is a gray solid, m.p.=96–97° C. $^1$H NMR (500 MHz, DMSO-d$_6$): δ 7.08 (s, 1H), 6.83 (s, 1H), 3.78 (s, 3H), 2.68 (t, 2H), 2.50 (t, 2H).

Example 2

Solid Phase Preparation of Representative Benzo[b]furan dimers

TABLE 1

Building Blocks for Scheme IV

| Side Chains | 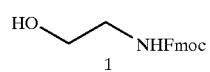 | 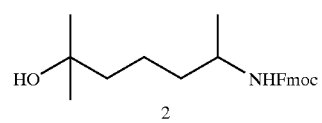 |
|---|---|---|
| | 1 | 2 |
| Substrates | 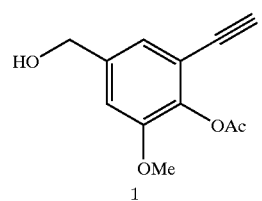 | 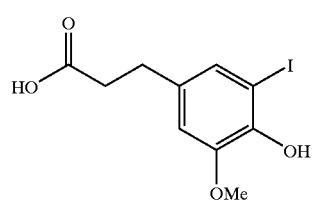 |
| | 1 | 2 |

TABLE 1-continued
Building Blocks for Scheme IV
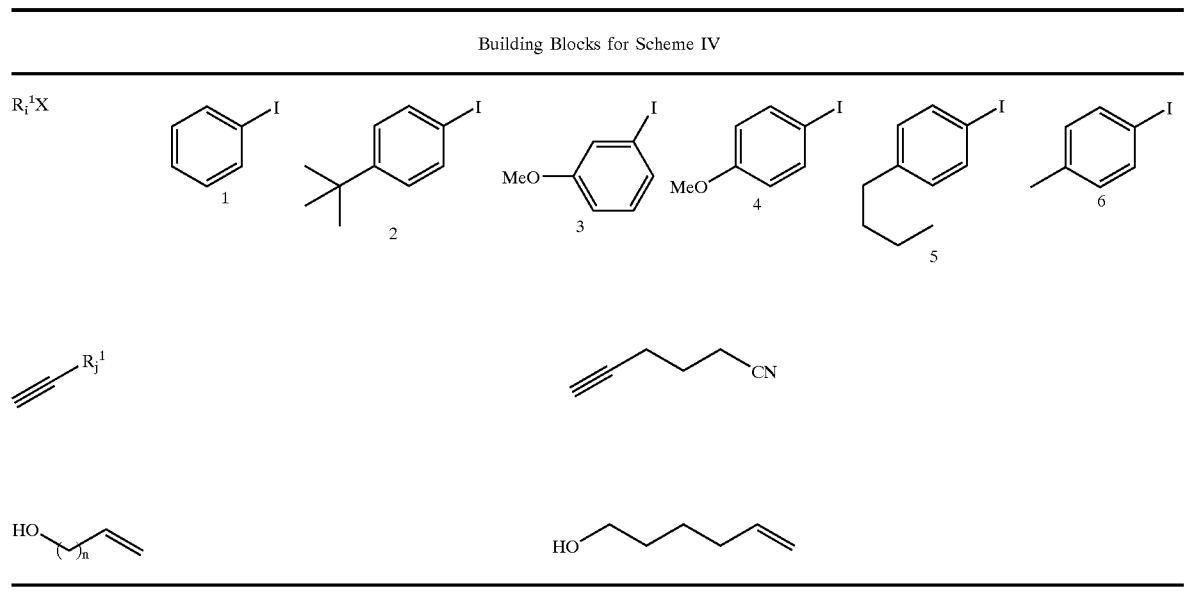
Scheme 4:
Constructing C2/S2 Symmetric 2,3-distributed Benzol[b]furan Scaffold
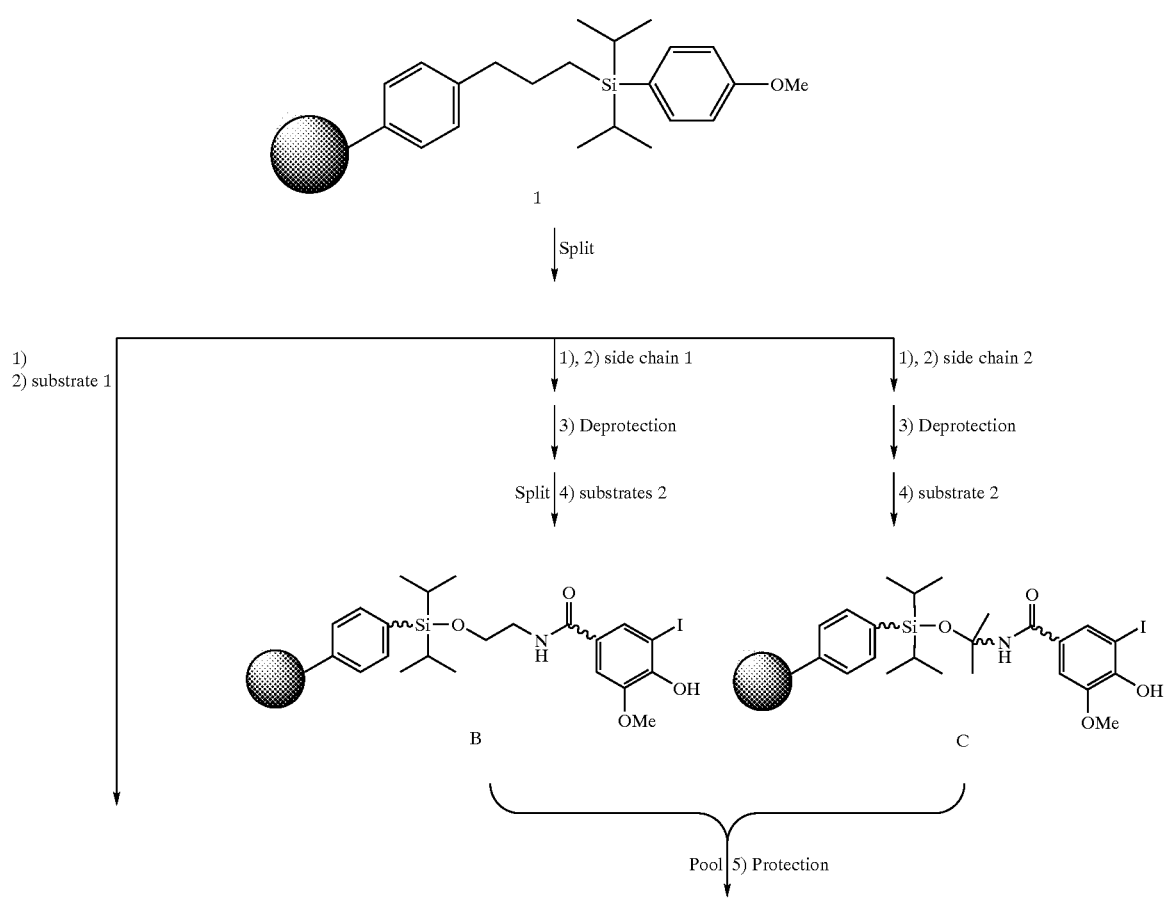

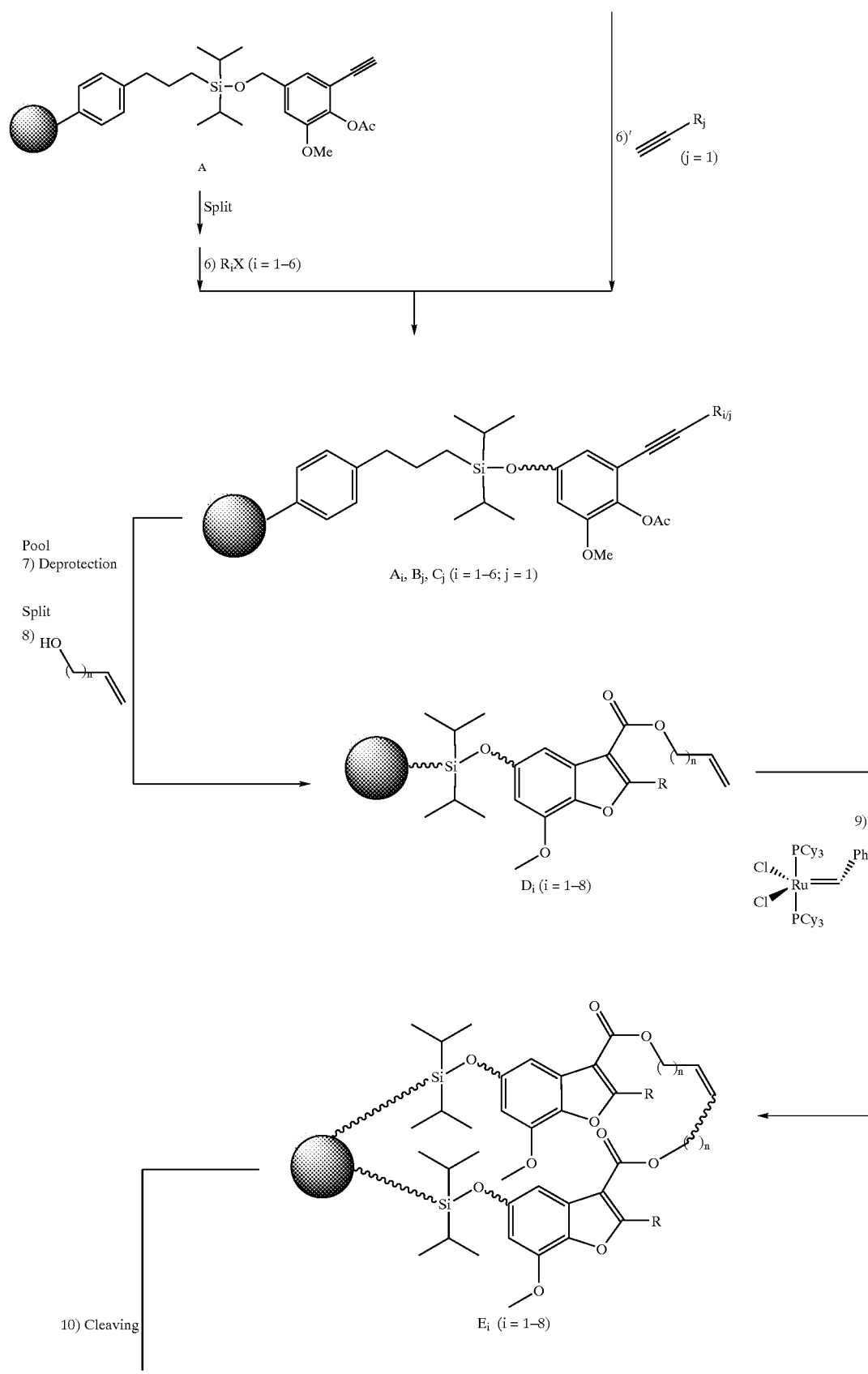

-continued

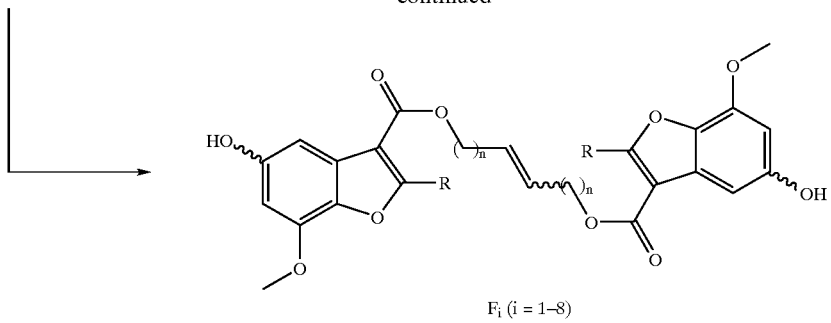

F$_i$ (i = 1–8)

Conditions: 1) Me$_3$SiCl, imidazole, CH$_2$Cl$_2$, rt, 2 h; TfOH, CH$_2$Cl$_2$, rt, 1.5 h. 2) 2,6-lutidine, CH$_2$Cl$_2$, rt, 4 h. 3) piperidine, DMF, rt, 1 h. 4) Py-BOP, NMM, DMF/THF 1/2, rt, 12 h. 5)Ac$_2$O, LiCl, CH$_2$Cl$_2$, rt, 10 h. 6) X=OTf, Pd(PPh$_3$)$_4$, CuI, DIPEA, DMF/THF 1/1, rt, 24 h; X=I, fresh Pd$^0$ (0.3 eq), CuI, DIPEA, DMF/THF 1/1, rt, 24 h, or Pd$_2$(dba)$_3$ (5%), CuI, NEt$_3$, rt, 48 h. 6)' Pd(PPh$_3$)$_2$Cl$_2$ (0.3 eq), CuI, DIPEA, CH3CN, rt, 24 h. 7) NH$_2$NH$_2$/THF. (0.1 M). 8) CO, R$_2$OH, Pd(PPh$_3$)$_2$Cl$_2$-dppp (1.2 eq), CsOAc, DMF, 45° C., 48 h. 9) Grubbs catalyst (10%), CH$_2$Cl$_2$, 24 h. 10) HF/Py 5% in THF, rt, 1 h; TMSOMe, 0.5 h.

General Procedure for Linking the Starting Materials onto the Beads

On-bead substrate A (Scheme IV): Dichloromethane (100 mL) was added to the mixture of macrobeads I (1 g, 1.4 mmol/g, 1.4 mmol) and imidazole (60 mg, 0.88 mmol) in a 25 mL of fritted glass tube with Teflon cap, followed by addition of trimethylsilyl chloride (0.1 mL, 0.79 mmol) at room temperature. After 2 h of shaking, the reaction mixture was filtered under the protection of Ar and the beads were washed with dry dichloromethane (2×10 mL). The beads were then suspended in dry dichloromethane (10 mL), and treated with TfOH (1 mL, 6 mmol) in dry CH$_2$Cl$_2$ (10 mL) and shaken for another 1.5 h at room temperature. The reaction mixture was filtrated under Ar, and washed with dry CH$_2$Cl$_2$ (2×10 mL). The beads were suspended in dry CH$_2$Cl$_2$ (10 mL), followed by addition of substrate 1 (600 mg, 2.7 mmol) and 2,6-lutidine (0.5 mL, 4.3 mmol). The reaction mixture was kept shaking at room temperature for 4 h. The reaction mixture was filtered, followed by washing with a sequence of CH$_2$Cl$_2$, DMF, MeOH, DMF and CH$_2$Cl$_2$ (2 h for each washing with 20 mL of individual solvent) to give the on-bead compound A in almost quantitative yield (confirmed by the analysis of a nano-probe MAS-$^1$H NMR for substrate A. Therefore, the loading level for the on bead compound A could be regarded as 1.25 mmol/g based on the theoretical calculation (1.4 mmol/{1+1.4[FW(A)–FW(I)]/1000} g=1.4/[1+1.4(220–108)/1000]=1.2 mmol/g). Gel-phase MAS-$^1$H-NMR (500 MHz, 3 beads used, CD$_2$Cl$_2$ δ 5.20): δ 4.60 (s, 2H), 3.60 (s, 3H), 3.09 (s, 1H), 2.16(s, 3H), 0.94 (s, 12 H, 2 isopropyl groups attached to Si). (Elemental analysis of the beads I gave 3.91% Si by weight, which equals to 1.4 mmol/g.). Cleavage of 10–20 beads by HF/Pyr in THF and drying (see Standard Cleavage and drying procedure) gave the cleaved substrate A. $^1$H NMR (500 MHz, CDCl$_3$): δ 7.11 (s, 1H), 7.05 (s, 1H), 4.68 (s, 2H), 3.87 (s, 3H), 3.23 (s, 1H), 2.38(s, 3H). LC-MS (4.0 min, [M+1]$^+$. 221 (APCI+)). HRMS (FAB) m/z calcd for C$_{12}$H$_{12}$O$_4$ 220.0736; found 220.0732.

On-bead substrates B and C (Scheme IV): The procedure for the Steps from 1) to 2) was similar to the preparation of on-bead substrate A. The loading levels were calculated as 1.0 mmol/g based on the UV absorption of the cleaved Fmoc. The Fmoc was removed by shaking the beads in piperidine and DMF (25% v/v, 60 eq) at rt for 1 h. The reaction mixture was filtered, washed and dried. The dried beads (each 100 mg, 0.1 mmol), substrate 2 (0.12 mmol), Py-BOP (each 43 mg, 0.11 mmol) and NMM(4-methylmorpholine) (each 0.015 mL, 0.13 mmol) were mixed with THF/DMF (2:1, each 5 mL) and the mixture was rotated at rt over night. Each reaction mixture was filtered, and washed sequentially with CH$_2$Cl$_2$, DMF, MeOH, DMF and CH$_2$Cl$_2$ (2 h for each washing with 20 mL of individual solvent) and dried to give the on-bead substrates B and C. 10–20 beads from each substrate were cleaved and then dried (see Standard Cleavage and drying procedure) to give the cleaved substrates respectively for analysis. Further acylation was carried out by mixing each potion of the dried beads with acetic anhydride (0.075 mL, 1 mmol), LiCl (2 mg, 0.05 mmol) in dry pyridine (0.15 mL) and CH$_2$Cl$_2$ (4 mL), and each reaction mixture was shaken overnight. After filtration of the reaction mixtures, each potion of the beads was washed sequentially with CH$_2$Cl$_2$, DMF, MeOH, DMF and CH$_2$Cl$_2$ (2 h for each washing with 100 mL of individual solvent) and dried.

B

4-Acetoxy-3-methoxy-5-iodo-N-(2-hydroxyethyl) benzene propanamide (B): $^1$H NMR (500 MHz, d$_6$-DMSO): δ 7.40 (m, 1H), 7.24 (d, 1 H, J=2.0 Hz), 6.98 (d, 1H, J=2.0 Hz), 3.74 (s, 3H), 3.38 (t, 2H, J=6.0 Hz), 3.12 (t, 2H, J=6.0 Hz), 2.78 (t, 2H, J=7.5 Hz), 2.40 (t, 2H, J=7.5 Hz), 2.28(s, 3H). LC-MS (4.65 min, [M+1]$^+$. 408 (APCI+)). HRMS (ES+) m/z calcd for C$_{14}$H$_{19}$INO$_5$ 408.0308; found 408.0292.

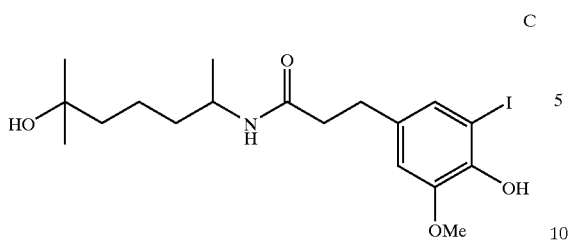

4-Hydroxy-3-methoxy-5-iodo-N-(1,5-dimethyl-5-hydroxyhexyl)benzenepropanamide (C): $^1$H NMR (500 MHz, d$_6$-DMSO): δ 9.20 (s, 1H), 7.60 (d, 1H, J=10.0 Hz), 7.06 (s, 1H), 6.80 (s, 1H), 3.78 (s, 3H), 2.67 (m, 2H), 2.29 (m, 2H), 1.20–1.30 (m, 6H), 1.04 (s, 4H), 0.98 (d, 2H, J=6.0 Hz). LC-MS (4.96 min, [M+1]$^+$. 666 (APCI+)).

General Procedure for the On-Bead Sonogashira Cross-Coupling Reaction:

a. General Procedure for the Sonogashira Cross-Coupling Reaction between the On-Bead Terminal Alkyne A and Various Aryl Iodides.

Phenyl acetylene (2.5 eq), Pd(PPh$_3$)$_2$Cl$_2$ (0.3 eq), CuI (0.4 eq), DIPEA (di-iso-propylethylamine) (25.0 eq) and DMF/THF (1:1, anhydrous) were mixed and the mixture was shaken at room temperature for 2 h. After addition of the aryl iodide (20 eq), the reaction mixture was kept shaking for another 2 h until the phenyl acetylene had reacted as determined by TLC. The beads A (1.0 eq) in MicroKans were then mixed with the aforementioned reaction mixture in dry box and the reaction mixture was kept shaking for another 24 h. The reaction mixture was filtered, washed (see Standard Washing Procedure) and dried. The intermediate for analysis was cleaved from 10–20 beads by HF/Pyr (5% in THF, 0.2 mL) at room temperature for 1 h, followed by quenching with TMS-OMe (see Standard Cleavage and drying procedure). The cleaving reagents were removed under high vacuum.

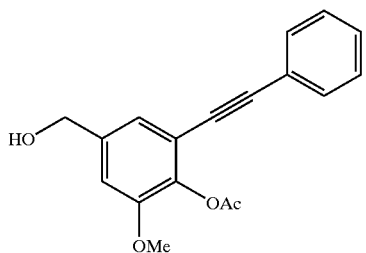

4-Acetoxy-3-methoxy-5-(phenylethynyl)benzyl alcohol (A1): $^1$H NMR (500 MHz, DMSO-d$_6$): δ 7.50 (m, 2H), 7.40 (m, 3H), 7.14 (s, 1H), 7.11 (s, 1H), 5.33 (t, 1H, J=6.0 Hz), 4.5 (d, 2H, J=6.0 Hz), 3.80 (s, 3H), 2.34 (s, 3H). LC-MS (6.33 min, [M+1]$^+$. 297 (APCI+)). HRMS (FAB) m/z calcd for C$_{18}$H$_{16}$O$_4$ 296.1049; found 296.1049.

The relative purity of compound A1 to the homo-dimer of the substrate A is 93.1%. [based on the corresponding $^1$H NMR integration, 100/(100+14.8/2)%=93.1%.

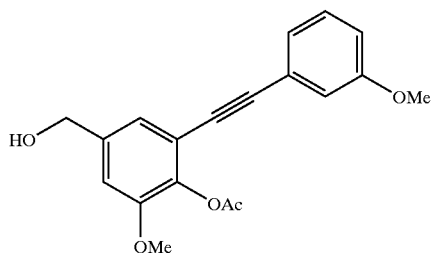

4-Acetoxy-5-[(4-t-butylphenyl)ethynyl]-3-methoxy benzyl alcohol (A2): $^1$H NMR (500 MHz, CDCl$_3$): δ 7.46 (s, 4H), 7.13 (s, 1H), 7.10 (s, 1H), 5.32 (t, 1H, J=6.0 Hz), 4.72 (d, 2H, J=6.0 Hz), 3.80 (s, 3H), 2.32 (s, 3H), 1.29 (s, 9H). LC-MS (7.56 min, [M+1]$^+$. 311 (APCI+)).

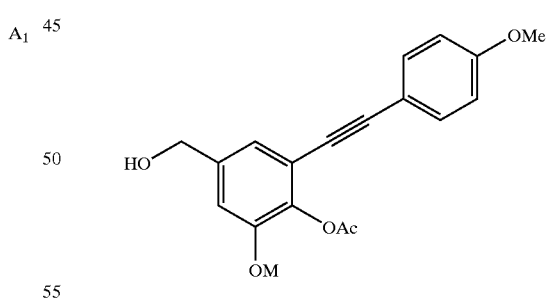

4-Acetoxy-3-methoxy-5-[(3-methoxyphenyl)ethynyl] benzyl alcohol (A3): $^1$H NMR (500 MHz, DMSO-d$_6$): δ 7.35 (t, 1H, J=8.0 Hz), 7.0–7.2 (m, 5H), 5.33 (t, 1H, J=6.0 Hz), 4.50 (d, 2H, J=6.0 Hz), 3.80 (s, 3H), 3.79 (s, 3H), 2.34 (s, 3H). LC-MS (6.40 min, [M+1]$^+$. 327 (APCI+)). HRMS (FAB) m/z calcd for C19H18O5 326.1154; found 326.1148. The relative purity of compound A3 to the homo-dimer of the substrate A is 94.2%. [based on the corresponding $^1$H NMR integration, 100/(100+12.3/2)%=94.2%.

4-Acetoxy-3-methoxy-5-[(4-methoxyphenyl)ethynyl] benzyl alcohol (A4): $^1$H NMR (500 MHz, DMSO-d$_6$): δ 7.46 (d, 2H, J=9.0 Hz), 7.11 (s, 1 H), 7.08 (s, 1 H), 6.99 (d, 2 H, J=9.0 Hz), 5.31 (t, 1H, J=6.0 Hz), 4.50 (d, 2H, J=6.0 Hz), 3.80 (s, 3H), 3.79 (s, 3H), 2.33 (s, 3H). LC-MS (6.29 min, [M+1]$^+$. 327 (APCI+)). HRMS (FAB) m/z calcd for C$_{19}$H$_{18}$O$_5$ 326.1154; found 326.1160.

The relative purity of compound A4 to the homo-dimer of the substrate A is 94.2% based on the corresponding $^1$H NMR integration, 100/(100+12.4/2)%=94.2%.

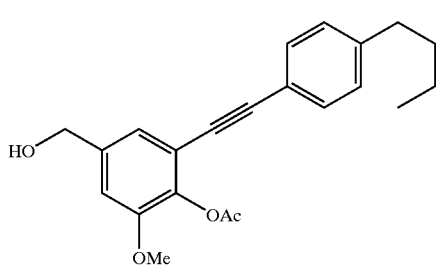

A5

4-Acetoxy-3-methoxy-5-(4-n-butylphenylethynyl)benzyl alcohol (A5): $^1$H NMR (500 MHz, DMSO-d$_6$): δ 7.42 (d, 2H, J=8.5 Hz), 7.26 (d, 2H, J=8.5 Hz), 7.13 (s, 1H), 7.10 (s, 1H), 5.32 (t, 1H, J=6.0 Hz), 4.50 (d, 2H, J=6.0 Hz), 3.84 (s, 3H), 2.61 (t, 2H, J=7.5 Hz), 2.32 (s, 3H).1.58 (m, 2H), 1.35 (m, 2H), 0.90 (t, 3H, J=7.5 Hz). LC-MS (8.63 min, [M+1]$^+$. 353 (APCI+)). HRMS (FAB) m/z calcd for $C_{22}H_{24}O_4$ 352.1675; found 352.1681.

The relative purity of compound A5 to the homo-dimer of the substrate A is 91.9% based on the corresponding $^1$H NMR integration, 100/(100+17.5/2)%=91.9%.

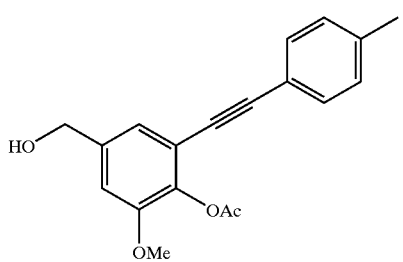

A6

4-Acetoxy-3-methoxy-5-(4-methylphenylethynyl)benzyl alcohol (A6): $^1$H NMR (500 MHz, CDCl$_3$): δ 7.40 (d, 2H, J=8.0 Hz), 7.17 (d, 2H, J=8.0 Hz), 7.14 (s, 1H), 7.02 (s, 1H), 4.70 (s, 2H), 3.88 (s, 3H), 2.39 (s, 3H). LC-MS (6.89 min, [M+1]$^+$. 311 (APCI+)). HRMS (FAB) m/z calcd for $C_{19}H_{18}O_4$ 310.1205; found 310.1205.

The relative purity of compound A6 to the homo-dimer of the substrate A is 89.4% based on the corresponding $^1$H NMR integration, 100/(100+23.7/2)%=89.4%.

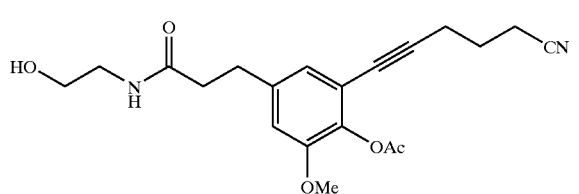

B1

4-Acetoxy-3-methoxy-5-(5-cyanopentynyl)propynyl]-N-(2-hydroxyethyl)-benzenepropanamide (B1): $^1$H NMR (500 MHz, d$_6$-DMSO): δ 6.98 (s, 1H), 6.87 (s, 1H), 4.64 (t, 1H, J=6.0 Hz), 3.75 (s, 3H), 3.37 (t, 2H, J=6.0 Hz), 3.11 (m, 2H), 2.77 (t, 2H, J=7.5 Hz), 2.60 (t, 2H, J=7.5 Hz), 2.54 (t, 2H, J=7.5 Hz), 2.40 (t, 2H, J=7.5 Hz), 2.28 (s, 3H), 1.82 (m, 2H). LC-MS (4.14 min, [M+1]$^+$. 373 (APCI+)). HRMS (ES) for $[C_{20}H_{25}N_2O_5+H]^+$, m/z calcd 373.1763, found: 373.1768.

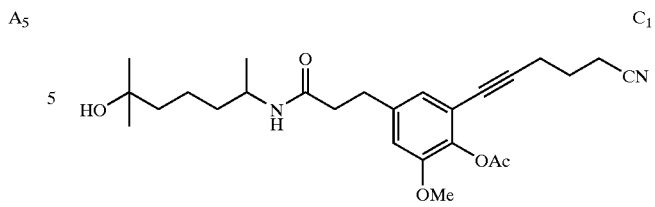

C1 b. General Procedure for the Sonogashira Cross-Coupling Reaction between the On-Bead Aryl Iodide B and C with Terminal Alkyne.

The beads B and C (1 eq) in Microkans separately, Pd(PPh$_3$)$_2$Cl$_2$ (0.3 eq), CuI (0.45 eq), DIPEA (15 eq) were mixed in DMF/THF (1:1, anhydrous), followed by addition of the corresponding acetylene (5.0 eq). The reaction mixture was shaken at room temperature for 24 h, and filtered, washed (see Standard Washing Procedure) and dried to give Bj and Cj. The intermediates for analysis were cleaved from 10–20 beads by HF/Pyr (5% in THF, 0.2 mL) at room temperature for 1 h, followed by quenching with TMS-OMe (see Standard Cleavage and drying procedure). The cleaving reagents were removed under high vacuum.

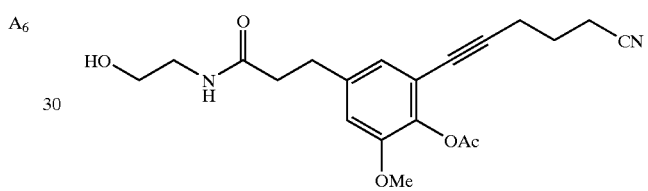

B1

4-Acetoxy-3-methoxy-5-(5-cyano-1-pentynyl)-N-(2-hydroxyethyl)-benzenepropanamide (B$_1$): $^1$H NMR (500 MHz, d$_6$-DMSO): δ 6.98 (s, 1H), 6.87 (s, 1H), 4.64 (t, 1H, J=6.0 Hz), 3.75 (s, 3H), 3.37 (t, 2H, J=6.0 Hz), 3.11 (m, 2H), 2.77 (t, 2H, J=7.5 Hz), 2.60 (t, 2H, J=7.5 Hz), 2.54 (t, 2H, J=7.5 Hz), 2.40 (t, 2H, J=7.5 Hz), 2.28 (s, 3H), 1.82 (m, 2H). LC-MS (4.14 min, [M+1]$^+$. 373 (APCI+)). HRMS (ES) for $[C_{20}H_{25}N_2O_5+H]^+$, m/z calcd 373.1763, found: 373.1768.

C1

4-Acetoxy-3-methoxy-5-(5-cyano-1-pentynyl)-N-(1,5-dimethyl-5-hydroxyhexyl) benzenepropanamide (C$_1$): $^1$H NMR (500 MHz, d$_6$-DMSO): δ 7.60 (d, 1H, J=7.0 Hz), 6.97 (s, 1H), 6.87 (s, 1H), 4.04 (s, 1H), 3.75 (s, 3H), 2.78 (t, 2H, J=7.0 Hz), 2.60 (t, 2H, J=7.0 Hz), 2.37 (m, 2H), 2.27 (s, 3H), 1.82 (m, 2H), 1.26 (m, 6H), 1.04 (s, 6H), 0.97 (d, 3H, J=6.0 Hz). LC-MS (5.46 min, [M–H$_2$O+1]$^+$. 440 (APCI+)).

Deprotection of the Acetates

The beads Ai, Bj, Cj and anhydrous hydrazine (0.5 M in THF) were mixed and rotated at rt for 2 h, and then filtered, washed (see Standard Washing Procedure) and dried.

Carbonylative Annulation (Stoichiometric Method).

Pd(PPh$_3$)$_2$Cl$_2$ (1.1 eq), dppp (1.1 eq) and CsOAc (20 eq) were mixed and degassed under high vacuum with CO for 3 times followed by adding the dry DMF and 5-hexen-1-ol (10:1), and the mixture was stirred at 45° C. under balloon pressure of CO for 30 min. Then the beads (1 eq) in Microkans were added. 24 hr later, the mixture was filtered and washed extensively, cleaved and dried to give Di.

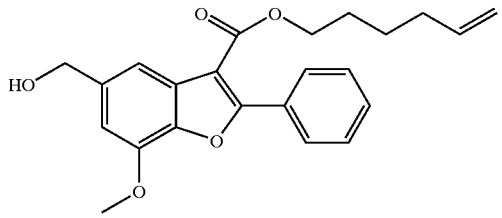

D₁

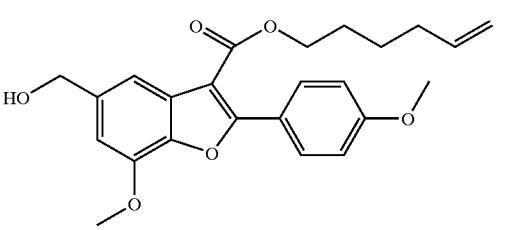

D₄

5-Hexen-1-yl 2-phenyl-5-hydroxymethyl-7-methoxy-benzot[b]furan-3-carboxylate (D1): ¹H NMR (500 MHz, d₆-DMSO): δ 7.91 (m, 2H), 7.54 (m, 3H), 7.39 (s, 1H), 7.01 (s, 1H), 5.78 (m,1H), 5.30 (t, 1H, J=6.0 Hz), 4.96 (m,2H), 4.60 (d, 1H, J=6.0 Hz), 4.27 (t, 2H, J=6.5 Hz), 3.96 (s, 3H), 2.03 (m, 2H), 1.66 (m, 2H), 1.39 (m, 2H). LC-MS (6.24 min, [M−H₂O+1]⁺. 363 (ES+)).

5-Hexen-1-yl 2-(4-methoxyphenyl)-5-hydroxymethyl-7-methoxy-benzo[b]furan-3-carboxylate (D4): δ 7.91 (d, 2H, J=9.0 Hz), 7.51 (s, 1H), 7.07 (d, 2H, J=9.0 Hz), 6.98 (s, 1H), 5.78 (m, 1H), 4.96 (m,2H), 4.59 (d, 1H, J=5.0 Hz), 4.28 (t, 2H, J=6.5 Hz), 3.95 (s, 3H), 3.84 (s, 3H), 2.04 (m, 2H), 1.66 (m, 2H), 1.42 (m, 2H). LC-MS (6.18 min, [M−H₂O+1]⁺. 393 (ES+)).

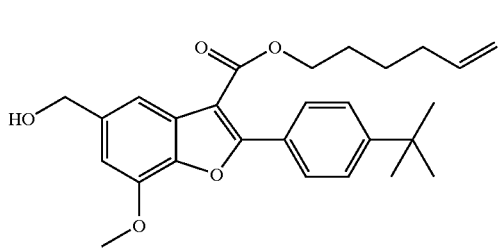

D₂

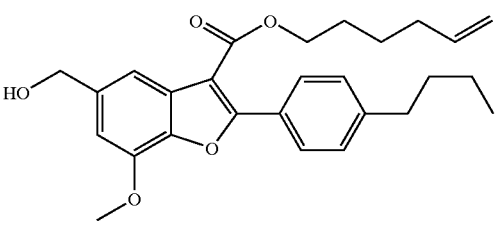

D₅

5-Hexen-1-yl 2-(4-t-butylphenyl)-5-hydroxymethyl-7-methoxy-benzo[b]furan-3-carboxylate (D2): 1H NMR (500 MHz, d₆-DMSO): δ 7.86 (d, 2H, J=7.5 Hz), 7.56 (d, 2H, J=7.5 Hz), 7.52 (s, 1H), 6.99 (s, 1H), 5.78 (m,1H), 4.96 (m,2H), 4.59 (s, 1H), 4.28 (t, 2H, J=6.5 Hz), 3.96 (s, 3H), 2.03 (m, 2H), 1.66 (m, 2H), 1.41 (m, 2H), 1.33 (s, 9H). LC-MS (7.24 min, [M+1]⁺. 437 (ES+)).

5-Hexen-1-yl 2-(4-n-butylphenyl)-5-hydroxymethyl-7-methoxy-benzo[b]furan-3-carboxylate (D5): δ 7.83 (d, 2H, J=8.5 Hz), 7.52 (s, 1H), 7.34 (d, 2H, J=8.5 Hz), 6.99 (s, 1H), 5.78 (m, 1H), 5.30 (t, 1H, J=6.0 Hz), 4.96 (m,2H), 4.59 (d, 1H, J=5.5 Hz), 4.27 (t, 2H J=6.0 Hz), 3.95 (s, 3H), 2.66 (m, 2H), 2.04 (m, 2H), 1.66 (m, 2H), 1.60 (m, 2H), 1.50 (m, 2H), 1.42 (m, 2H), 1.33 (m, 3H). LC-MS (7.41 min, [M+1]⁺. 437 (ES+)).

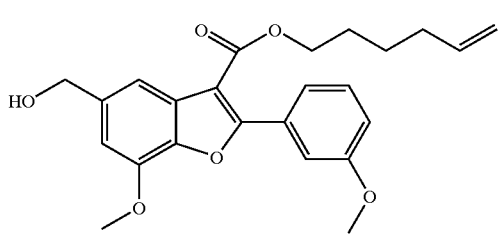

D₃

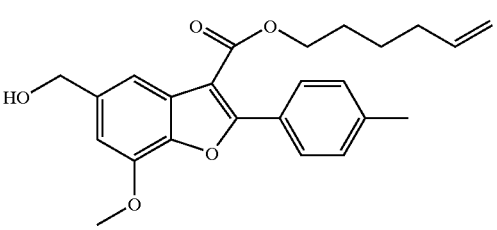

D₆

5-Hexen-1-yl 2-(3-methoxyphenyl)-5-hydroxymethyl-7-methoxy-benzo[b]furan-3-carboxylate (D3): ¹H NMR (500 MHz, d₆-DMSO): δ 7.40–7.60 (m, 4H), 7.13 (d, 2H, J=8.5 Hz), 5.78 (m,1H), 4.96 (m,2H), 4.59 (s, 1H), 4.27 (t, 2H, J=6.5 Hz), 3.96 (s, 3H), 3.82 (s, 3H), 2.03 (m, 2H), 1.66 (m, 2H), 1.39 (m, 2H). LC-MS (6.20 min, [M−H2O+1]⁺. 393 (ES+)).

5-Hexen-1-yl 2-(4-methylphenyl)-5-hydroxymethyl-7-methoxy-benzo[b]furan-3-carboxylate (D6): δ 7.82 (d, 2H, J=9.0 Hz), 7.52 (s, 1H), 7.34 (d, 2H, J=9.0 Hz), 6.99 (s, 1H), 5.78 (m,1H), 4.96 (m,2H), 4.59 (s, 1H), 4.27 (t, 2H, J=6.5 Hz), 3.95 (s, 3H), 2.39 (s, 3H), 2.03 (m, 2H), 1.66 (m, 2H), 1.39 (m, 2H). LC-MS (6.54 min, [M−H20+1]⁺. 377 (ES+)).

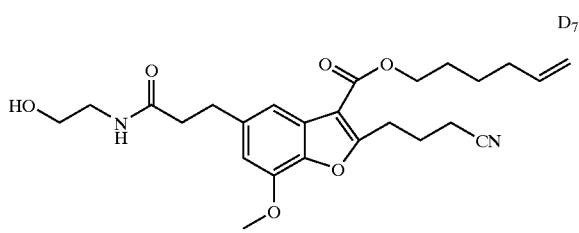

2-(3-Cyanopropyl)-3-(hex-5-enyl-1-oxy)carbonyl-7-methoxy-N-(2-hydroxyethyl)-benzo[b]furan-5-propanamide (D7): $^1$H NMR (500 MHz, $d_6$-DMSO): δ 7.83 (t, 1H, J=7.0 Hz), 7.28 (s, 1H), 6.84 (s, 1H), 5.78 (m,1H), 4.98 (m,2H), 4.59 (br, 1H), 4.30 (t, 2H, J=6.5 Hz), 3.91 (s, 3H), 3.23 (t, 2H, J=7.5 Hz), 3.09 (m, 2H), 2.88 (t, 2H, J=8.0 Hz), 2.58 (t, 2H, J=7.5 Hz), 2.40 (t, 2H, J=8.0 Hz), 2.09 (t, 2H, J=7.5 Hz), 1.97 (m, 2H), 1.75 (m, 2H), 1.51 (m, 2H). LC-MS (5.00 min, [M+1]$^+$. 457 (ES+)).

General Procedure for On-Bead Olefin Homo-Metathesis

The on-bead intermediates Di in MicroKan (27.5 mg, 27.5 μmol) and Grubbs catalyst (2.2 mg, 0.1 eq) in dry $CH_2Cl_2$ (15 mL) were mixed together and heated up to 40° C. for 24 h under protection of Argon, and then filtered, washed (see Standard Washing Procedure) and dried to give Ej. The final products Fi for analysis were cleaved from 10 beads by HF/Pyr (5% in THF, 0.2 mL) at room temperature for 1 h, followed by quenching with TMS-OMe (see Standard Cleavage and drying procedure). The cleaving reagents were removed under high vacuum.

The E/Z ratio of the final dimeric products mixtures were estimated by $^1$H NMR integration of the peaks around 5–6 ppm. The NMR analysis of our model synthetic study in solution phase confirmed that the alkenyl protons of the E-isomers of the following kind of scaffolds will show up at 5.36 ppm for products F1–F6 and 5.45 ppm for F7 and F8.

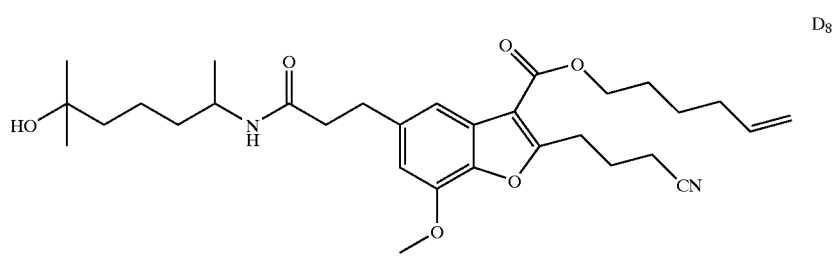

2-(3-Cyanopropyl)-3-(hex-5-enyl-1-oxy)carbonyl-7-methoxy-N-(1,5-dimethyl-5-hydroxyhexyl)benzo[b]furan-5-propanamide (D8): $^1$H NMR (500 MHz, $d_6$-DMSO): δ 7.28 (s, 1H), 6.84 (s, 1H), 5.78 (m,1H), 4.98 (m,2H), 4.30 (t, 2H, J=6.0 Hz), 3.91 (s, 3H), 3.22 (t, 2H, J=7.5 Hz), 2.88 (t, 2H, J=7.5 Hz), 2.58 (t, 2H, J=7.0 Hz), 2.37 (m, 2H), 2.10 (m, 2H), 1.98 (m, 2H), 1.75 (m, 2H), 1.52 (m, 2H), 1.20 (m, 9H),. LC-MS (5.58 min, [M+Na]$^+$. 463 (ES+)).

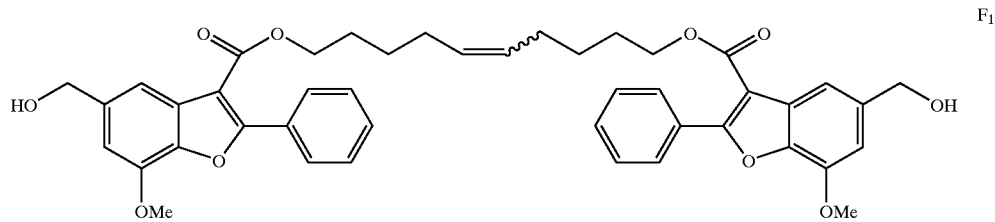

The Dimer $F_1$: $^1$H NMR (500 MHz, $d_6$-DMSO): δ 7.88 (m, 4H), 7.50 (m, 6H), 7.39 (s, 2H), 6.98 (s, 2H), 5.36 (m, 0.7H), 4.57 (s, 4H), 4.24 (t, 4H, J=6.5 Hz), 3.94 (s, 6H), 1.97 (m, 4H), 1.64 (m, 4H), 1.34 (m, 4H). LC-MS (7.08 min, [M-2H2O+1]$^+$. 697 (ES+)), E/Z(2:1).

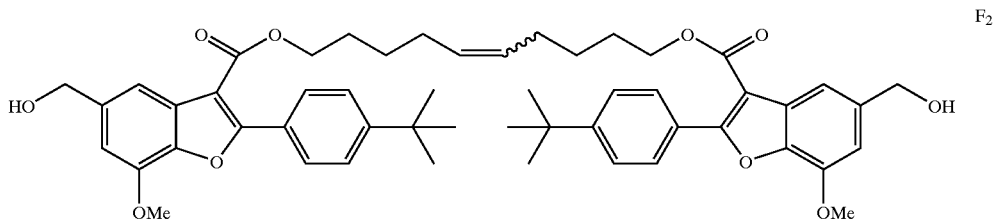
F₂
The Dimer F₂: ¹H NMR (500 MHz, d₆-DMSO): δ 7.83 (d, 4H, J=8.0 Hz), 7.50 (m, 6H), 6.96 (s, 2H), 5.36 (m, 0.6H), 4.57 (d, 4H, J=4.5 Hz), 4.24 (t, 4H, J=6.5 Hz), 3.94 (s, 6H), 1.97 (m, 4H), 1.64 (m, 4H), 1.20–1.40 (m, 22H). LC-MS (8.25 min, [M+Na+1]⁺. 868 (ES+)), E/Z (3:2).
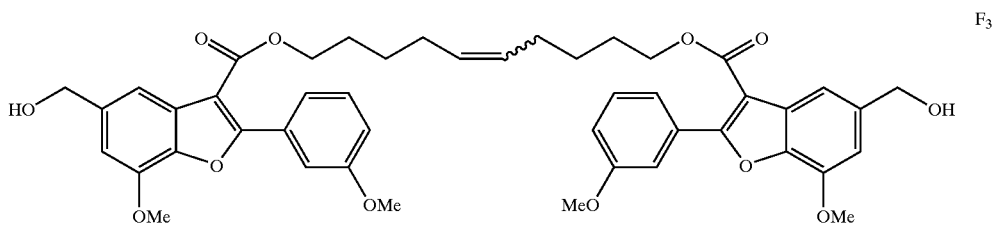
F₃
The Dimer F₃: ¹H NMR (500 MHz, d₆-DMSO): δ 7.40–7.60 (m, 8H), 7.09 (m, 2H), 6.98 (s, 2H), 5.36 (m, 0.5H), 4.57 (d, 4H, J=4.0 Hz), 4.24 (t, 4H, J=6.5 Hz), 3.94 (s, 6H), 3.80 (s, 6H), 1.96 (m, 4H), 1.63 (m, 4H), 1.32 (m, 4H), LC-MS (6.94 min, [M-2H₂O+2H]⁺. 758 (ES+), [M+Na+1]⁺. 816 (ES+)), E/Z (1:1).
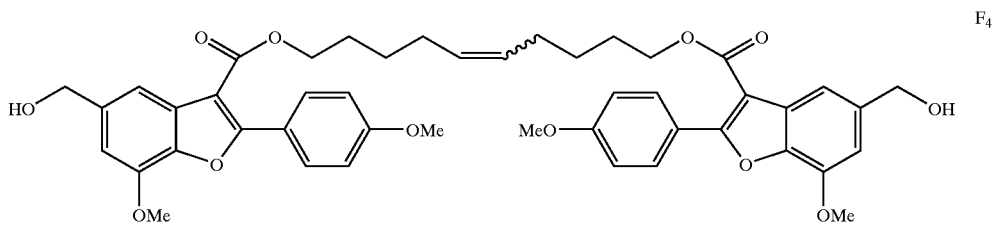
F₄
The Dimer F₄: ¹H NMR (500 MHz, d₆-DMSO): δ 7.88 (d, 4H, J=8.5 Hz), 7.50 (s, 2H), 7.05 (d, 4H, J=8.5 Hz), 6.96 (s, 2H), 5.36 (m, 1H), 4.57 (s, 4H), 4.24 (t, 4H, J=6.5 Hz), 3.93 (s, 6H), 3.82 (s, 6H), 1.97 (m, 4H), 1.64 (m, 4H), 1.28 (m, 4H), LC-MS (6.88 min, [M-2H₂O+2H]⁺. 758 (ES+), [M+Na+1]⁺. 816 (ES+)), E/Z (10:1).
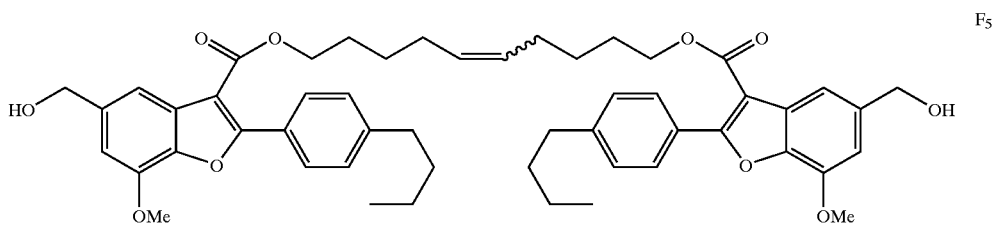
F₅

The Dimer F$_5$: $^1$H NMR (500 MHz, d$_6$-DMSO): δ 7.80 (d, 4H, J=8.5 Hz), 7.50 (s, 2H), 7.31 (d, 4H, J=8.5 Hz), 6.96 (s, 2H), 5.36 (m, 1H), 4.57 (s, 4H), 4.24 (t, 4H, J=6.5 Hz), 3.93 (s, 6H), 3.82 (s, 6H), 2.62 (m, 4H), 1.97 (m, 4H), 1.10–1.80 (m, 22H), LC-MS (6.88 min, [M–2H$_2$O+2H]$^+$. 810 (ES+), [M+Na+1]$^+$. 868 (ES+)), E/Z (10:1).

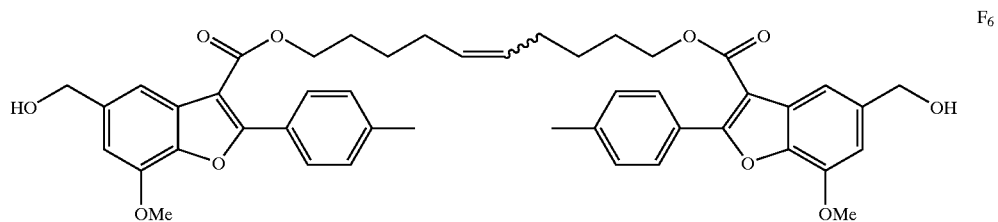

F$_6$

The Dimer F$_6$: $^1$H NMR (500 MHz, d$_6$-DMSO): δ 7.80 (d, 4H, J=7.5 Hz), 7.50 (s, 2H), 7.31 (d, 4H, J=7.5 Hz), 6.96 (s, 2H), 5.36 (m, 1H), 4.57 (s, 4H), 4.24 (t, 4H, J=6.5 Hz), 3.93 (s, 6H), 2.36 (m, 6H), 1.97 (m, 4H), 1.64 (m, 4H), 1.35 (m, 4H), LC-MS (7.45 min, [M–2H$_2$O+2H]$^+$. 726 (ES+), [M+Na+1]$^+$. 784 (ES+)), E/Z (10:1).

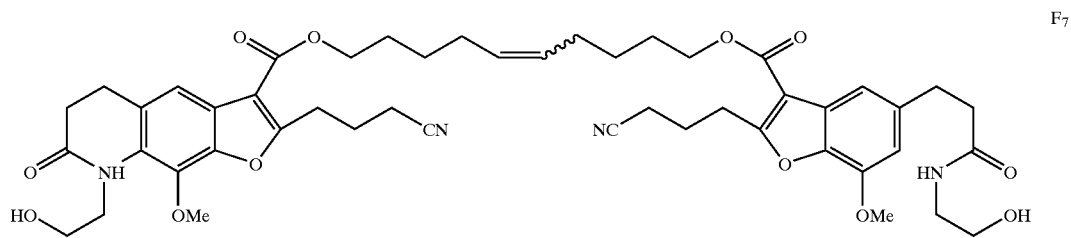

F$_7$

The Dimer F$_7$: $^1$H NMR (500 MHz, d$_6$-DMSO): δ 7.83 (s, 2H), 7.26 (s, 2H), 6.82 (s, 2H), 5.45 (m, 0.5H), 4.57 (s, 4H), 4.24 (m, 4H), 3.90 (s, 6H), 3.22 (m, 4H), 3.10 (m, 4H), 2.87 (t, 4H, J=8.0 Hz), 2.56 (t, 4H, J=7.0 Hz), 2.39 (t, 4H, J=8.0 Hz), 1.97 (m, 4H), 1.64 (m, 4H), 1.35 (m, 4H). LC-MS (5.10 min, [M+2H]$^+$. 886 (ES+), E/Z (1:1).

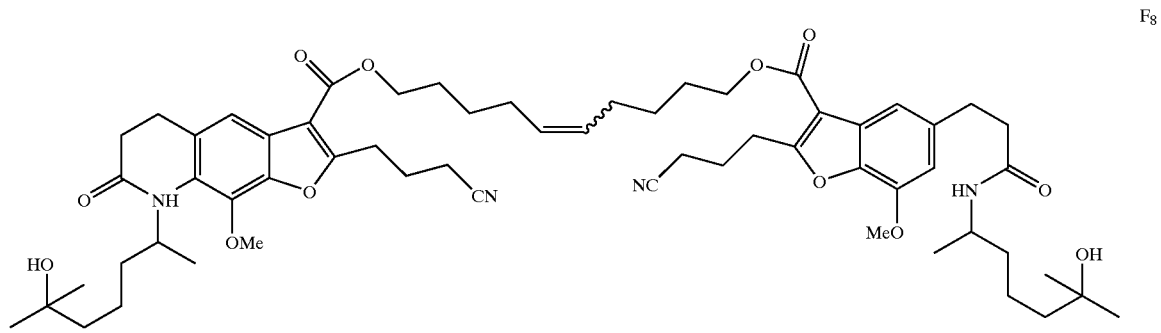

F$_8$

The Dimer F$_8$: $^1$H NMR (500 MHz, d$_6$-DMSO): δ 7.59 (m, 2H), 7.26 (s, 2H), 6.81 (s, 2H), 5.45 (m, 0.35H), 4.24 (m, 2H), 4.02 (m, 2H), 3.89 (s, 6H), 3.70 (m, 4H), 3.20 (m, 4H), 2.85 (m, 4H), 2.58 (m, 4H), 2.38 (m, 4H), 1.90–2.10 (m, 8H), 1.60–1.80 (m, 8H), 0.90–1.10 (m, 18H). LC-MS (5.92 min, [M+2H]$^+$. 1054 (ES+), E/Z (1:2).

Example 3

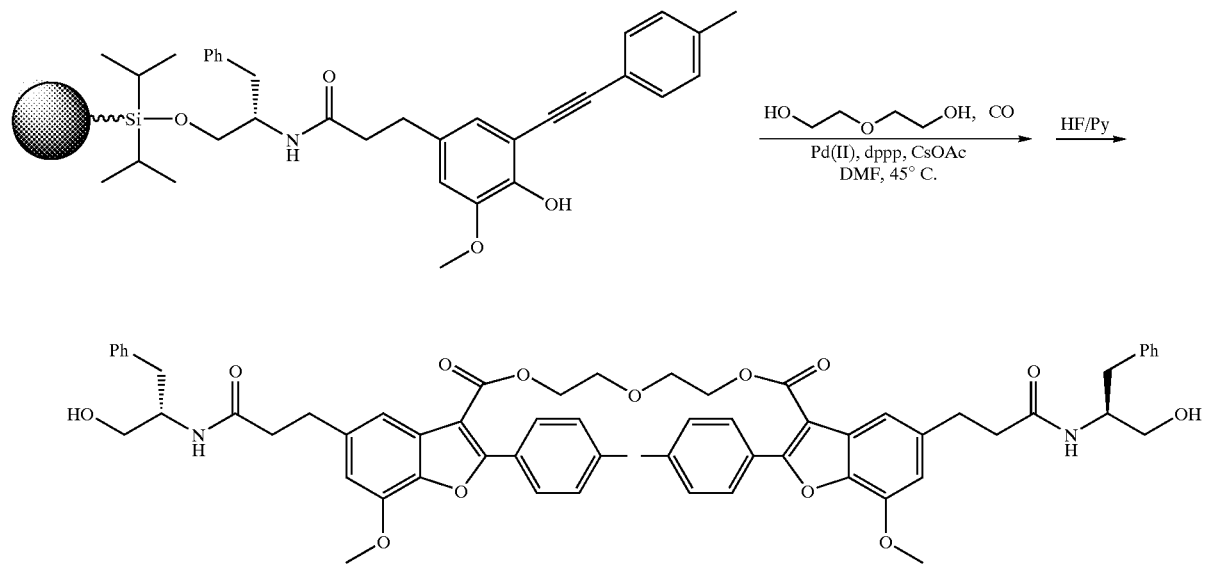

Pd(PPh$_3$)$_2$Cl$_2$ (1.1 eq), dppp (1.1 eq) and CsOAc (20 eq) were mixed and degassed under high vacuum with CO for 3 times followed by adding the dry DMF and ethylene diol (10:1), and the mixture was stirred at 45° C. under balloon pressure of CO for 30 min. Then the beads (1 eq) in Microkans were added. 24 hr later, the mixture was filtered and washed extensively, cleaved and dried to give (see Standard Cleavage and drying procedure). The cleaving reagents were removed under high vacuum.

Example 4

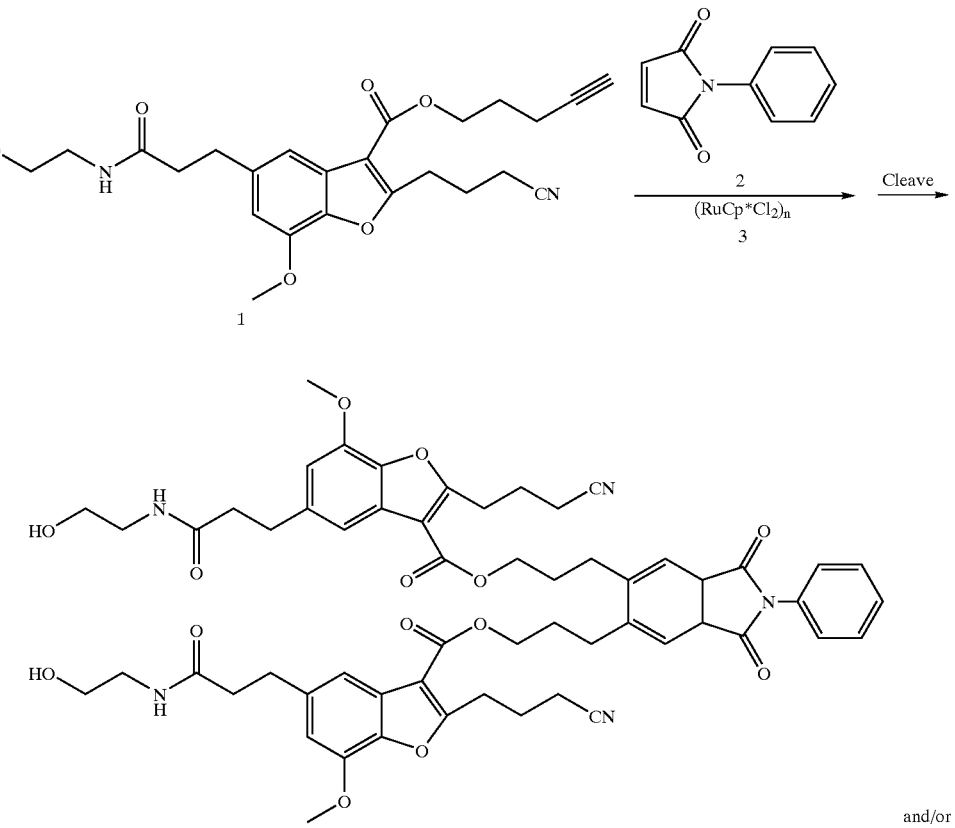

-continued
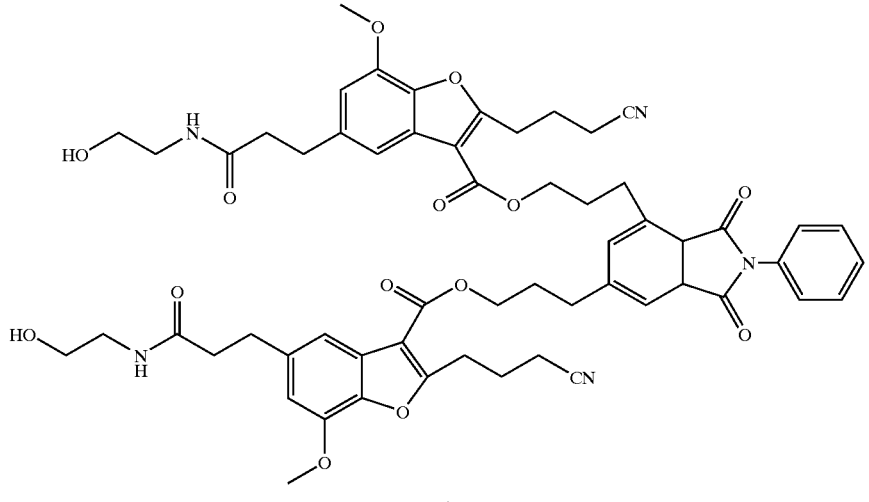
4
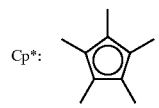
Cp*:
The on-bead substrate 1 (1 equiv), N-phenylmaleimide 2 (1.2 equiv) and Ru(III) catalyst 3 (0.1 equiv) were mixed in degassed $CH_2Cl_2$ and shaken at room temperature for 12 hours. Then the mixtures were washed, dried and cleaved to generate the target product 4. 80% conversion, $[M-2H_2O+1]^{+\cdot}$ 1018, $[M-H_2O+1]^{+\cdot}$ 1036, $[M+H]^{+\cdot}$ 1054, $[M+Na]^{+\cdot}$ 1076.
Example 5
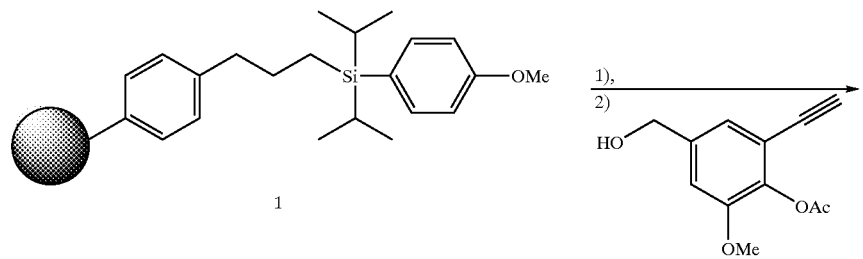
1
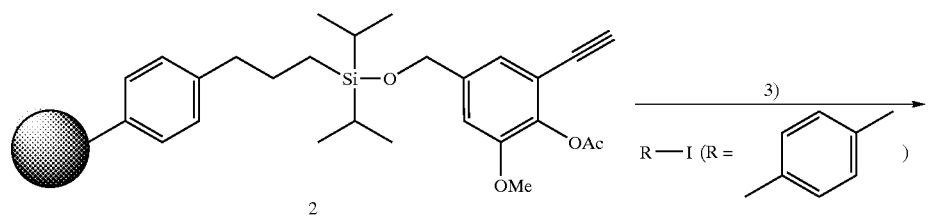
2
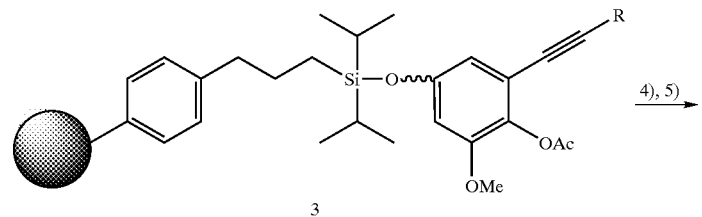
3

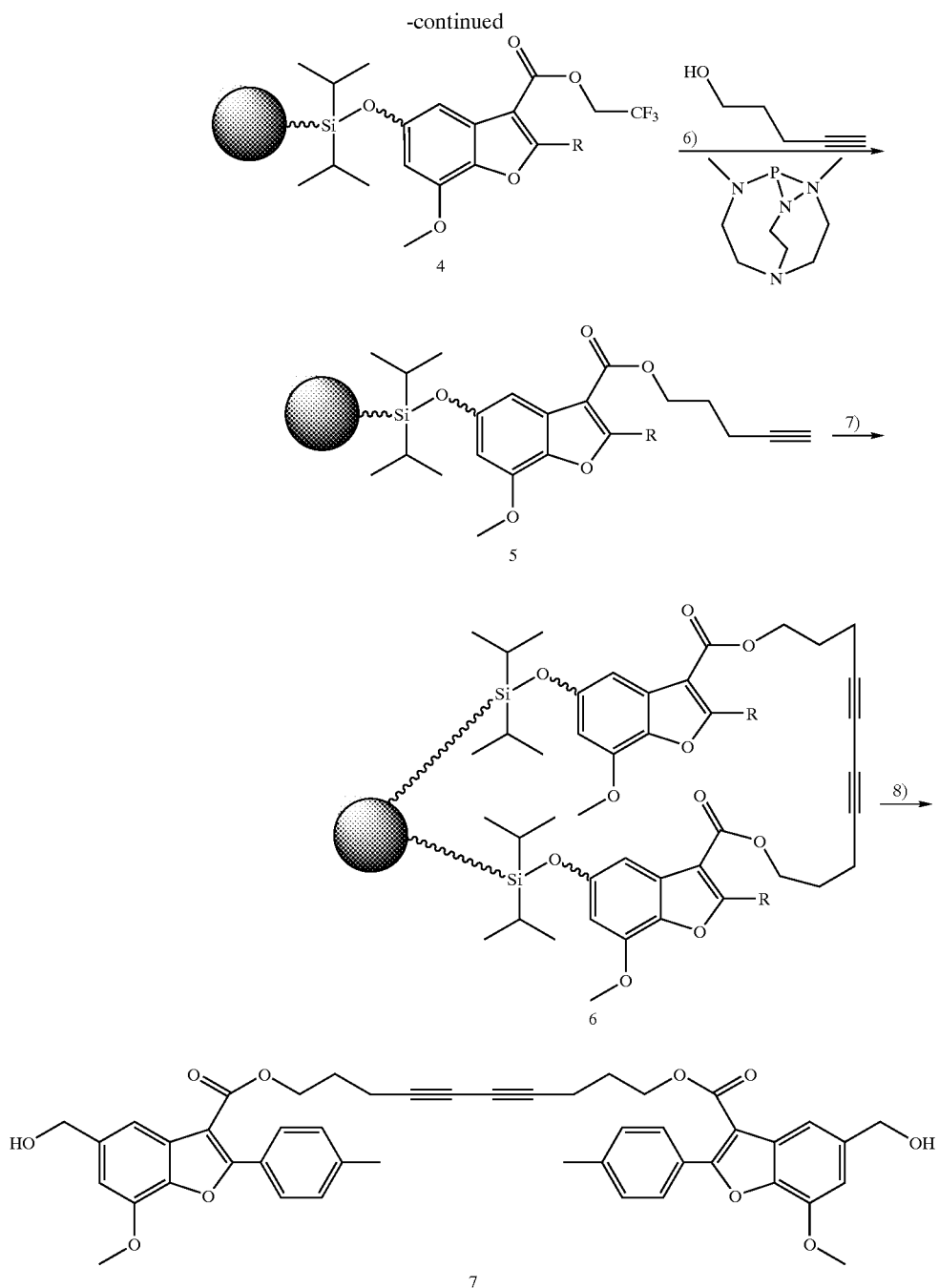

Conditions: 1) Me₃SiCl, imidazole, CH₂Cl₂, rt, 2 h; TfOH, 2) 2,6-lutidine, CH₂Cl₂, rt, 4 h. 3) Pd₂(dba)₃ (5%), CuI, NEt₃, rt, 48 h. 4) NH₂NH₂/THF. (0.1 M). 5) CO, CF₃CH₂OH, Pd(PPh₃)₂Cl₂-dppp (1.2 eq), CsOAc, DMF, 45° C., 48 h. 6) THF, 24 h. 7) Cu(I)/Cu(II)/Ag(I), DBU/ TMEDA, CH₂Cl₂, rt, 1.5 h. 8) HF/Py 5% in THF, rt, 1 h; TMSOMe, 0.5 h.

General Procedures:

The procedures from the step 1) to 5) and 8) are the same as those of the Example 2. The procedure for the step 6): Beads 4 (1 equiv.), 4-pentyn-1-ol (20 equiv.), 2,8,9-Trimethyl-2,5,8,9-tetraaza-1-phosphabicyclo[3.3.3] undecane (0.1 equiv.) and DMF/THF (1:1) were mixed together and shaken at r.t. for 24 hrs. The procedure for the step 7): The on-bead acetylenes 5 (1 equiv.), CuI (0.05 equiv.), CuCl₂ (0.05 equiv.), N,N,N,N-Tetramethylethylenediamine (0.05 equiv.) and DBU (20 equiv.) were mixed together and dried under high vacuum for 30 minutes and then dry dichloromethane was added. The whole mixtures were shaken for 12 hrs. at r.t. Work-up and cleaving the target sample from the beads for analysis are according to the standard procedures described before in this patent. Analysis of Product 7. ¹H NMR (500 MHz, d6-DMSO): δ 7.80 (d, 4H, J=8.0 Hz), 7.5 (s, 2 H), 7.80 (d, 4H, J=8.0 Hz), 6.99 (s, 2H), 5.29 (t, 2H, J=6.0 Hz), 4.58 (t, 4H, J=6.0 Hz), 4.29 (t, 4H, J=6.0 Hz), 3.94 (s, 6H), 2.30 (s, 6H), 2.31 (t, 4H, J=6.0 Hz), 1.85 (m, 4H). LC-MS (6.91 min, [M+Na]⁺. 777 (ES+)).

What is claimed is:
1. A compound of the formula I

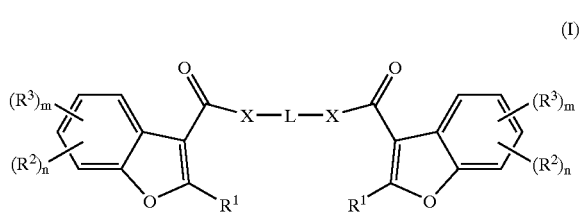

wherein

L is selected from —(CH$_2$)$_a$—, and a group of the formula

—B—A—B— wherein a is selected from 2–20,
B is —(CH$_2$)$_b$—, —(CH$_2$)$_c$—O—(CH$_2$)$_d$—, or

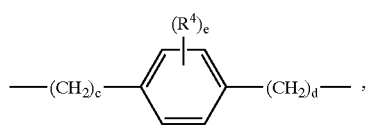

and

A is selected from a group of the formula

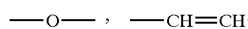

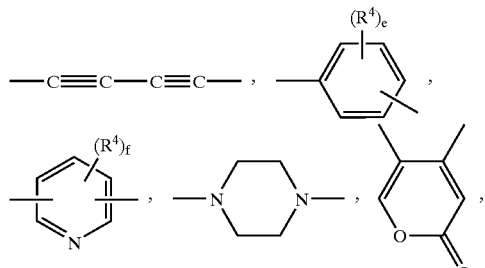

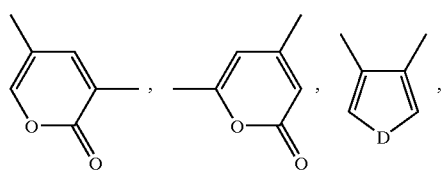

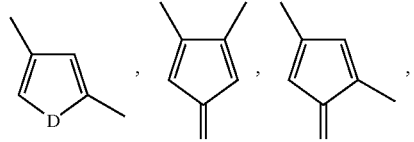

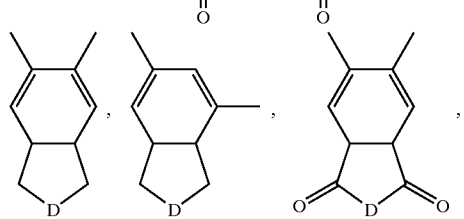

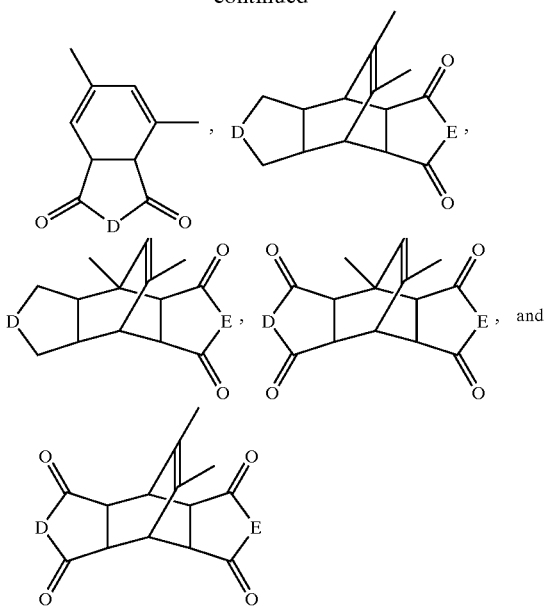

wherein R$^4$ is selected from halogen, lower alkyl, lower alkoxy, NO$_2$, and —NRR,
D and E are independently selected from O, S, Se, CRR and NR,
b is selected from 1–10,
c is selected from 1–8,
d is selected from 1–8,
e is selected from 0–4;
f is selected from 0–3, and
R is selected from H, lower alkyl, aralkyl and aryl;

X is selected from O, or —NH—;

R$^1$ is selected from
 a C$_1$–C$_{20}$ alkyl which may be unsubstituted or substituted with one or more substituents selected from CN, halogen, lower alkoxy, thio-lower alkyl, nitro, phosphinos, phosphates, and protected amino;
 a C$_1$–C$_{20}$ alkenyl which may be unsubstituted or substituted with one or more substituents selected from CN, halogen, lower alkoxy, thio-lower alkyl, nitro, phosphinos, phosphates, and protected amino;
 an aromatic group which may be unsubstituted or substituted with one or more substituents
  selected from halogen, lower alkyl, lower alkoxy, thio-lower alkyl, nitro, phosphinos, phosphates, and protected amino; and
 an aralkyl which may be unsubstituted or substituted with one or more substituents selected
  from halogen, lower alkyl, lower alkoxy, thio-lower alkyl, nitro, phosphinos, phosphates, and protected amino;

R$^2$ is selected from halogen, hydroxy, CN, nitro, lower alkyl, lower alkoxy, thio-lower alkyl, lower alkenyl, cycloalkyl, C$_2$–C$_8$ acyl, lower alkyl ester, and lower alkyl amide;

R$^3$ is a group of the formula

wherein Y and Z are independently selected from O, S, —OCH$_2$CH$_2$O—,

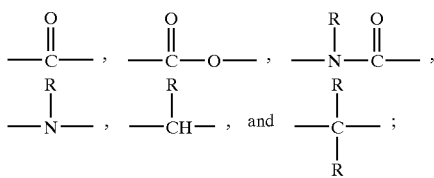

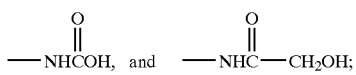

p, r and t are independently selected from values from 0 to 10;

q and s are independently selected from 0 and 1, provided that when t=0 then s=0, and when r=0 then q=0; and $R^5$ is selected from OH, $CO_2H$,

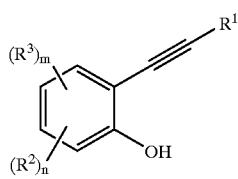

n is selected from 0–4; and m is 0 or 1, with the proviso that the sum of n plus m does not exceed 4.

2. A compound of the claim 1, wherein A is selected from a group of the formula —O—, —CH=CH—, and —C≡C—C≡C—.

3. A process for the preparation of a compound of the formula I

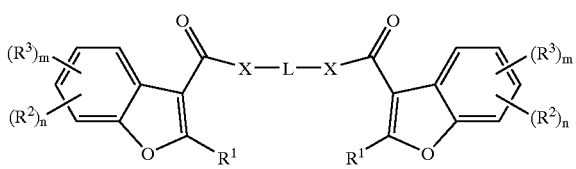

(I)

comprising the steps of (a) a Sonogashira reaction to prepare a compound of the formula III

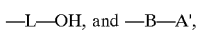

(III)

by reacting a compound of the formula IV

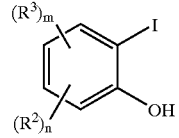

(IV)

with a terminal alkyne represented by the formula V:

(V)

in the presence of base and a transition metal catalyst;

(b) carbonylative annulation to give a compound of the formula II

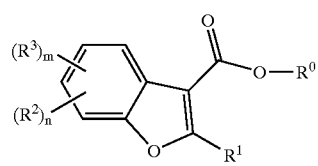

(II)

by treating a compound of the formula III with an alcohol of the formula $R^0$—OH in the presence of a transition metal catalyst, carbon monoxide and a base, wherein $R^0$ is lower alkyl, aralkyl, or aryl, wherein the lower alkyl, aralkyl, or aryl, may be optionally substituted with one or more halogen, CN and nitro, or $R^0$ is selected from a group of the formula —L—OH, and —B—A', wherein L and B are as described above for a compound of the formula I, and A' is —CH=$CH_2$ or —C≡CH ; and (c) coupling two molecules of the formula II to give a compound of the formula I, wherein $R^1$, $R^2$, $R^3$, X, L, n and m are as described in claim 1 for the compound of the formula I.

* * * * *